United States Patent [19]

Bell et al.

[11] Patent Number: 4,666,899
[45] Date of Patent: May 19, 1987

[54] 3-(OPTIONALLY SUBSTITUTED-BUT-1-EN-3-YNYL) CEPHALOSPORINS

[75] Inventors: Richard Bell, South Ruislip; Paul D. Hallam, West Drayton; Michael W. Foxton, Chalfont St. Giles, all of United Kingdom

[73] Assignee: Glaxo Group Limited, London, England

[21] Appl. No.: 732,094

[22] Filed: May 9, 1985

[30] Foreign Application Priority Data

May 10, 1984 [GB] United Kingdom ............... 8411954

[51] Int. Cl.$^4$ ............... A61K 31/545; C07D 501/18; C07D 501/22; C07D 501/24
[52] U.S. Cl. ............... 514/200; 514/202; 540/215; 540/217; 540/222
[58] Field of Search ............... 544/16, 17, 22; 514/200, 202; 540/215, 217, 222

[56] References Cited

U.S. PATENT DOCUMENTS

| 4,107,431 | 8/1978 | Clark | 544/22 |
| 4,520,022 | 5/1985 | Hoshi | 544/22 |
| 4,559,344 | 12/1985 | Takaya | 544/22 |

FOREIGN PATENT DOCUMENTS

| 1342241 | 1/1974 | United Kingdom . |
| 2130582 | 7/1984 | United Kingdom ............... 544/16 |

Primary Examiner—Sam Rosen
Assistant Examiner—Robert Benson
Attorney, Agent, or Firm—Bacon & Thomas

[57] ABSTRACT

Compounds of general formula I

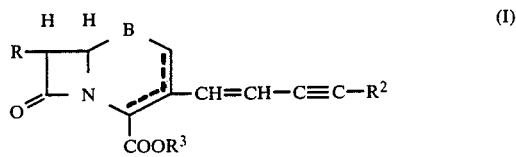

(wherein
R represents $NH_2$— or an acylated or silylated amino group;
$R^2$ represents a hydrogen, halogen, alkyl, aryl, carboxyl or lower alkoxycarbonyl group;
$R^3$ is hydrogen or a carboxyl blocking group;
B is $>S$ or $>S \rightarrow O$ ($\alpha$- or $\beta$-); and the dotted line represents $\Delta^2$ or $\Delta^3$ unsaturation) and salts, solvates and esters thereof are described.

Compounds where $R^3$ is hydrogen, the dotted line represents $\Delta^3$ unsaturation and R is a group of formula $R^a CH_2 CONH—$

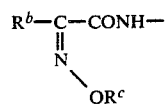

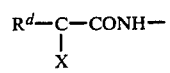

(where $R^a$ is an optionally substituted heterocyclic aryl group having one or more hetero atoms selected from S, N and O in the ring, $R^b$ is an optionally substituted aryl group, $R^c$ is hydrogen, acyl, alkyl, alkenyl, alkynyl, cycloalkyl, cycloalkylalkyl, aryl or aralkyl, $R^d$ is as defined for $R^a$ or is an optionally substituted group and X is amino, hydroxyl, acylated hydroxyl, carboxyl or esterified carboxyl)
and especially the compounds in which B is $>S$, have valuable antibiotic activities.

Compounds in which the $—CH=CH—C\equiv C—R^2$ group is in the trans configuration have been found to have good oral absorption.

The remaining compounds of formula (I) are valuable as intermediates in processes for the preparation of the above active antibiotics, which processes are also described.

8 Claims, No Drawings

3-(OPTIONALLY SUBSTITUTED-BUT-1-EN-3-YNYL) CEPHALOSPORINS

This invention relates to improvements in or relating to cephalosporins. More particularly it relates to new cephalosporin compounds and derivatives thereof having valuable antibiotic activity.

The cephalosporin compounds in this specification are named with reference to "cepham" after *J.Amer.- Chem. Soc.*, 1962, 84, 3400, the term "cephem" referring to the basic cepham structure with one double bond.

Cephalosporin antibiotics are widely used in the treatment of diseases caused by pathogenic bacteria in human beings and animals, and are especially useful in the treatment of diseases caused by bacteria which are resistant to other antibiotics such as penicillin compounds, and in the treatment of penicillin-sensitive patients. In many instances it is desirable to employ a cephalosporin antibiotic which exhibits activity against both gram-positive and gram-negative microorganisms, and a significant amount of research has been directed to the development of various types of broad spectrum cephalosporin antibiotics.

Our British Patent Specification No. 1342241 describes a class of cephalosporin antibiotics characterised in that they are substituted at the 3-position by a vinyl group which may optionally be substituted by a substituted or unsubstituted aliphatic, cycloaliphatic, aromatic or araliphatic group.

Our British Patent Specification No. 1399086 describes a novel class of cephalosporin antibiotics containing a 7β-(α-etherified oximino)acylamido group, the oximino group having the syn configuration. This class of antibiotic compounds is characterised by high antibacterial activity against a range of gram-positive and gram-negative organisms coupled with particularly high stability to β-lactamases produced by various gram-negative organisms. The 3-substituent of the cephalosporin compounds may be inter alia an optionally substituted vinyl group.

Our British Patent Specification No. 1496757 relates to cephalosporin antibiotics having a 7β-(syn-α-etherified oximino)acylamido group, in which the etherifying group is substituted by a carboxyl group. The 3-substituent may be inter alia an optionally substituted vinyl group, and compounds are exemplified which have a 3-(2-methoxycarbonyl)vinyl or 3-(2-cyano)vinyl group.

European Patent Application No. 30630 discloses cephalosporin antibiotics having at the 3-position an unsubstituted vinyl group and a wide range of possible substituents in the 7β-position. One of the compounds claimed, namely (6R,7R)-7-[(Z)-2-(2-aminothiazol-4-yl)-2-(carboxymethoxyimino)acetamido]-3-ethenyl-ceph-3-em-4-carboxylate has been reported to have been successfully used in clinical trials in the treatment of humans by oral administration, although when administered orally to mice it has substantially no activity against strains of the gram positive organism *Staphylococcus aureus*. Furthermore its absorption from the gastrointestinal tract is only moderate, as is its pharmacokinetic half-life.

However, there is in general a need for a compound having good activity against both Gram-positive and Gram-negative organisms coupled with good oral absorption. We have now found certain novel 3-(optionally substituted but-1-en-3-ynyl)cephalosporin compounds which generally exhibit the desired advantageous properties. Protected forms of these compounds and precursors therefor are also valuable as intermediates in the production of the active antibiotics according to the invention.

Thus, according to one feature of the invention we provide compounds of general formula I

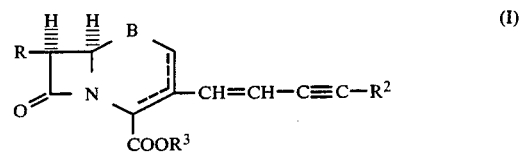

[wherein
R represents —NH$_2$ or an acylated or silylated amino group;
R$^2$ represents a hydrogen or halogen atom or an alkyl, aryl, carboxyl or lower alkoxycarbonyl group;
R$^3$ represents a hydrogen atom or a carboxyl blocking group;
B is >S or >S→O (α- or β-); and
the dotted line bridging the 2-, 3- and 4-positions indicates that the compound is a ceph-2-em or ceph-3-em compound]
and salts, solvates and esters thereof.

According to a further aspect of the invention we provide the cephalosporin antibiotics of formula (Ia)

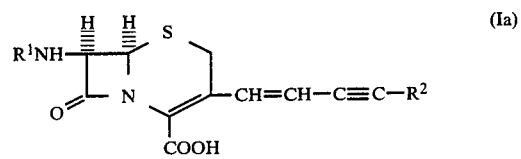

[wherein
R$^1$ is an acyl group selected from
(i) a group of formula R$^a$CH$_2$CO—, where R$^a$ is an optionally substituted 5- or 6-membered heterocyclic aryl group having one or more heteroatoms selected from S, N and O in the ring,
(ii) a group of formula

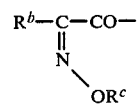

where R$^b$ is an optionally substituted carbocyclic or heterocyclic aryl group, and R$^c$ is a hydrogen atom, or an optionally substituted acyl, alkyl, alkenyl, alkynyl, cycloalkyl, cycloalkylalkyl, aryl (heterocyclic or carbocyclic), or aralkyl (heterocyclic or carbocyclic) group; and
(iii) a group of formula

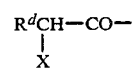

where R$^d$ is as defined above for R$^a$ or an optionally substituted carbocyclic group, and X is an amino, hydroxyl, acylated hydroxyl, carboxyl or esterified carboxyl group; and R² represents a hydrogen atom, a halogen atom, or an alkyl, aryl (carbocyclic or heterocyclic), carboxyl or lower alkoxycarbonyl group] and non-toxic salts, 1-oxides and non-toxic metabolically labile esters thereof.

The 1-oxides of the compounds of the invention may be in α- or β-form, but the sulphides of the compounds of the invention are preferred.

Where R¹ in compounds according the invention represents a group of formula

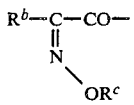

the compounds according to the invention are syn isomers with respect to the configuration of the oximino group. The syn isomeric form is defined by the configuration of the —OR$^c$ group with respect to the carboxamido group. In this specification, the syn configuration is denoted structurally as

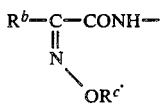

It will be understood that since the oxime group in the 7-side chain in such compounds of the invention results in geometrical isomerism, then some admixture with the corresponding anti isomer may occur.

It will further be appreciated that the compounds of the invention exist as geometrical isomers with respect to the 3-substituent. Thus, the substituents on the double bond may be in the cis i.e.

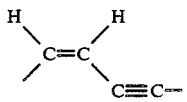

or trans i.e.

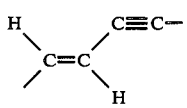

isomer forms. Both such geometrical isomers as well as mixtures thereof are intended to be within the scope of the invention.

Examples of heterocyclic aryl groups for R$^a$ include 3- and 4-isoxazolyl, tetrazolyl, thiazolyl, furyl, thienyl, isothiazolyl, thiadiazolyl, pyrazolyl, pyridyl, pyrimidinyl and oxadiazolyl. Such groups may optionally be substituted by, for example, one or more halogen atoms (e.g. chlorine, bromine or iodine), or nitro, hydroxyl, amino, lower (e.g. C$_{1-6}$) alkyl, lower (e.g. C$_{1-6}$) alkoxy or lower (e.g. C$_{2-6}$) acyloxy, e.g. alkanoyloxy, groups.

Preferred carbocyclic or heterocyclic aryl groups for R$^b$ include, for example, phenyl, thiazolyl, isothiazolyl, furyl, thienyl, thiadiazolyl, oxadiazolyl, pyridyl, pyrazinyl, pyridazinyl and pyrimidinyl. Such groups may optionally be substituted by, for example, one or more halogen atoms e.g. chlorine, bromine or iodine, or nitro, hydroxyl, amino, lower (e.g. C$_{1-6}$) alkyl, lower (e.g. C$_{1-6}$) alkoxy or lower (e.g. C$_{2-6}$) acyloxy e.g. alkanoyloxy, groups. A particularly preferred group for R$^b$ is 2-aminothiazol-4-yl.

Examples of the group R$^c$ include C$_{1-4}$alkyl (e.g. methyl, ethyl or prop-2-yl), C$_{2-4}$alkenyl (e.g. allyl), C$_{2-4}$alkynyl (e.g. propynyl), C$_{3-6}$cycloalkyl (e.g. cyclobutyl or cyclopentyl), C$_{3-6}$cycloalkyl C$_{1-4}$alkyl (e.g. cyclopropylmethyl), an aryl group such as phenyl or a 5- or 6-membered heterocyclic group containing at least one heteroatom selected from S, N and O such as thienyl, furyl or pyridyl, or an aralkyl group such as benzyl or fur-3-ylmethyl, or a C$_{2-6}$alkanoyl group such as acetyl.

The group R$^c$ may optionally be substituted, for example, by hydroxyl, alkoxy (e.g. methoxy), amino, substituted amino (e.g. methyl- or dimethylamino), nitro, carbamoyl, substituted carbamoyl (e.g. methyl- or dimethylcarbamoyl), carboxyl, esterified carboxyl (e.g. C$_{2-5}$alkoxycarbonyl such as methoxycarbonyl) and cyano groups, or by halogen atoms (e.g. chlorine, bromine or iodine). A particularly preferred group for R$^c$ is carboxymethyl.

Examples of the group R$^d$ include those listed above for the group R$^a$. In addition R$^d$ may, for example, be selected from phenyl, 4-hydroxyphenyl, cyclohexa-1,4-dien-1-yl, naphthyl and benzothienyl.

Examples of the group X include amino, acetoxy and ethoxycarbonyl groups.

Examples of the group R² include hydrogen, chloro, bromo, C$_{1-4}$alkyl (such as methyl or ethyl), phenyl, furyl, carboxyl or C$_{2-5}$alkoxycarbonyl such as methoxycarbonyl.

The compounds of the invention may exist in tautomeric forms (for example, where R$^b$ is a 2-aminothiazolyl group) and it will be understood that such tautomeric forms, e.g. the 2-iminothiazolyl form, are included within the scope of the invention.

The invention also includes within its scope the solvates (especially the hydrates) of the compounds of formula (Ia). It also includes within its scope the solvates of non-toxic salts of the compounds of formula (Ia) and non-toxic salts and solvates of non-toxic metabolically labile esters of the compounds of formula (Ia).

The compounds of formula (Ia) according to the invention exhibit antibacterial activity against a wide variety of gram-positive and gram-negative bacteria.

Compounds of formula (Ia) according to the invention have been found to exhibit high activity against various members of the Enterobacteriaceae (e.g. strains of *Escherichia coli, Klebsiella pneumoniae, Shigella sonnei, Enterobacter cloacae, Serratia marcescens, Citrobacter diversus,* Providence species, *Proteus mirabilis,* and especially indole-positive Proteus organisms such as *Proteus vulgaris* and *Proteus morganii*) and strains of *Haemophilus influenzae.* They are also active against gram-positive bacteria such as *Staphylococcus aureus.*

Compounds of formula (Ia) in the trans configuration have been found to be well absorbed on oral administration.

A preferred class of compounds according to the invention may be represented by the formula (Ib):

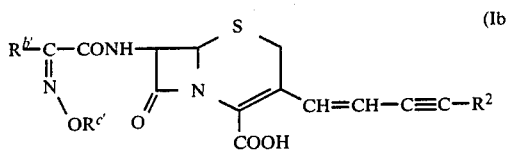

wherein $R^{b'}$ represents a thiazolyl, thiadiazolyl, furyl, thienyl or pyrimidyl group optionally substituted by one or more substitutents selected from amino or halo (chloro, bromo or iodo), $R^{c'}$ represents a hydrogen atom or a $C_{1-4}$alkyl, $C_{2-4}$alkenyl, $C_{2-4}$alkynyl, $C_{3-6}$cycloalkyl or $C_{3-6}$cycloalkyl-$C_{1-4}$alkyl group optionally substituted by carbamoyl, methylcarbamoyl, dimethylcarbamoyl, carboxyl, $C_{2-5}$alkoxycarbonyl or halo and $R^2$ represents a hydrogen atom or a $C_{1-4}$alkyl, phenyl, carboxyl or $C_{2-5}$alkoxycarbonyl group. The activity of these compounds against gram-negative bacteria such as those specified above is generally high and extends to many β-lactamase-producing gram-negative strains. The compounds also possess high stability to β-lactamases produced by a range of gram-positive and gram-negative organisms.

A more preferred class of compounds according to the invention may be represented by the formula (Ic):

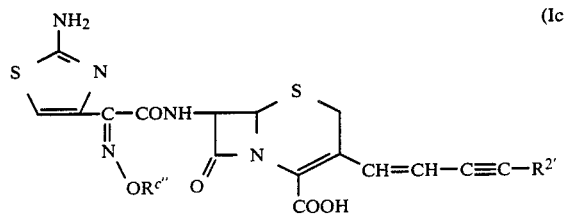

wherein $R^{c''}$ represents a hydrogen atom or a methyl, ethyl, carboxymethyl, 2-carboxyprop-2-yl, carbamoylmethyl or methoxycarbonylmethyl group and $R^{2'}$ represents a hydrogen atom or a $C_{1-4}$alkyl group (e.g. methyl or ethyl), and the non-toxic salts and non-toxic metabolically labile esters thereof.

Compounds of formula (Ic) have been found to possess good activity against a wide range of gram-positive and gram-negative bacteria.

Compounds of formula (Ic) in which the 3-substituent is in the trans configuration have been found to be well absorbed upon oral administration. Thus, the trans isomers and their non-toxic salts and non-toxic metabolically labile esters are more particularly preferred compounds of the invention.

Two compounds according to the invention which are particularly preferred on the basis of their good oral absorption and high antibacterial activity are:
(6R,7R)-7-[(Z)-2-(2-aminothiazol-4-yl)-2-(carboxymethoxyimino)acetamido]-3-[(E)-hex-1-en-3-ynyl]ceph-3-em-4-carboxylic acid; and
(6R,7R)-7-[(Z)-2-(2-aminothiazol-4-yl)-2-(carboxymethoxyimino)acetamido]-3-[(E)-but-1-en-3-ynyl)]ceph-3-em-4-carboxylic acid.

An outstanding compound according to the invention is (6R,7R)-7-[(Z)-2-(2-aminothiazol-4-yl)-2-(carboxymethoxyimino)acetamido]-3-[(E)-pent-1-en-3-ynyl]ceph-3-em-4-carboxylic acid which has the structural formula:

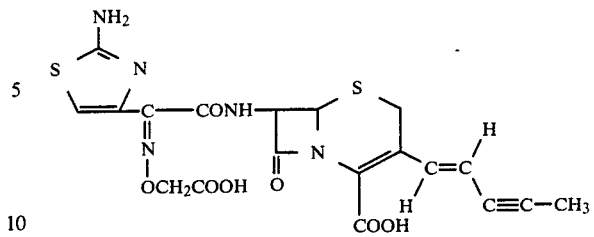

and the non-toxic salts and non-toxic metabolically labile esters thereof. Particular mention may be made of the sodium salt.

This compound possesses, both in vitro and in vivo, good activity against gram positive organisms and high activity against a broad spectrum of gram negative organisms. It is well absorbed upon oral administration and has been used successfully to treat experimental infections (e.g. *Escherichia coli* and *Staphylococcus aureus*) in small rodents by oral administration. Furthermore, it has been found to possess an unusually long pharmacokinetic half-life in mice and this means that less frequent dosing than normal may be possible. This combination of oral adsorption, good levels of broad spectrum antibacterial activity in vivo and long pharmacokinetic half-life is particularly surprising in that most cephalosporin antibiotics which have hitherto been available have not been effective upon oral administration and have required more frequent dosing.

Non toxic salt derivatives which may be formed by reaction of one or more carboxyl groups present in the compounds of formula (Ia) include inorganic base salts such as alkali metal salts (e.g. sodium and potassium salts) and alkaline earth metal salts (e.g. calcium salts); amino acid salts (e.g. lysine and arginine salts); organic base salts (e.g. procaine, phenylethylbenzylamine, dibenzylethylenediamine, ethanolamine, diethanolamine and N-methylglucosamine salts). Other non-toxic salt derivatives include acid addition salts where the compounds contain a basic group, e.g. formed with hydrochloric, hydrobromic, sulphuric, nitric, phosphoric, formic and trifluoroacetic acids. The salts may also be in the form of resinates formed with, for example, a polystyrene resin or cross-linked polystyrene divinylbenzene copolymer resin containing amino or quaternary amino groups or sulphonic acid groups, or with a resin containing carboxyl groups, e.g. a polyacrylic acid resin. Soluble base salts (e.g. alkali metal salts such as the sodium salt) of the compounds of formula (Ia) may be used in therapeutic applications because of the rapid distribution of such salts in the body upon administration. Where, however, insoluble salts of compounds (Ia) are desired in a particular application, e.g. for use in depot preparations, such salts may be formed in conventional manner, for example with appropriate organic amines.

These and other salt derivatives such as the salts with toluene-p-sulphonic and methanesulphonic acids may be employed as intermediates in the preparation and/or purification of the present compounds of formula (Ia), for example in the processes described below.

Non-toxic metabolically labile ester derivatives which may be formed by esterification of one or more carboxyl groups in the parent compounds of formula (Ia) include acyloxyalkyl esters, e.g. lower alkanoyloxymethyl or -ethyl esters such as acetoxy-methyl or -ethyl or pivaloyloxymethyl esters, and alkoxycarbonyloxyalkyl esters such as ethoxycarbonyloxyethyl esters. In addition to the above ester derivatives, the present invention includes within its scope the compounds of formula (Ia) in the form of other physiologically acceptable equivalents, i.e. physiologically acceptable compounds which, like the metabolically labile esters, are converted in vivo into the parent antibiotic compounds of formula (Ia).

The compounds of formula (Ia) according to the invention may be used for treating a variety of diseases caused by pathogenic bacteria in human beings and animals, such as respiratory tract infections and urinary tract infections.

According to a further aspect of the invention we provide a process for the preparation of compounds of general formula (I) as hereinbefore defined and salts, solvates and esters thereof, which comprises:

(A) (for the preparation of compounds wherein R represents an acylated amino group); acylating a compound of formula (I) or a salt thereof, wherein R represents an amino or silylated amino group; or (B) (for the preparation of compounds wherein R represents a silylated amino group); silylating a compound of formula I or a salt thereof, wherein R represents an amino group; or (C) reacting a compound of formula (IV)

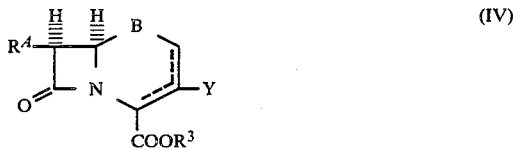

(IV)

wherein $R^3$, B and the dotted line are as hereinbefore defined; $R^4$ represents $NH_2$— or a silylated or acylated amino group or a protected form of said acylated amino group; and Y represents a substituent capable of reacting with one or more reagents to form or introduce a group of formula —CH=CH—C≡C—$R^2$ at the 3-position) with one or more said reagents.

According to a still further aspect of the invention we provide a process for the preparation of the cephalosporin antibiotics of formula (Ia) as hereinbefore defined and non-toxic salts, solvates, 1-oxides and non-toxic metabolically labile esters thereof, which process comprises:

($A^1$) acylating a compound of the formula

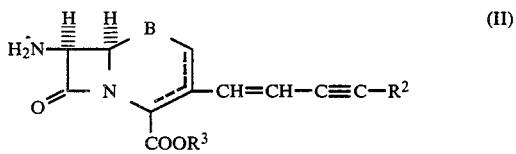

(II)

[wherein $R^2$ is as defined above, $R^3$ is a hydrogen atom or a carboxyl blocking group, e.g. the residue of an ester-forming aliphatic or araliphatic alcohol or an ester-forming phenol, silanol or stannanol (the said alcohol, phenol, silanol or stannanol preferably containing 1 to 20 carbon atoms); B is >S or >S→O (α- or β-); and the dotted line bridging the 2-, 3- and 4-positions indicates that the compound is a ceph-2-em or ceph-3-em compound] or a salt, e.g. an acid addition salt (formed with, for example, a mineral acid such as hydrochloric, hydrobromic, sulphuric, nitric or phosphoric acid or an organic acid such as methanesulphonic or toluene-p-sulphonic acid) or an N-silyl derivative thereof, with an acid of formula

$R^{14}COOH$ (III)

(wherein $R^{14}$ is as defined above for $R^1$ or is a protected form thereof) or with an acylating agent corresponding thereto;

($B^1$) reacting a compound of formula (IVa)

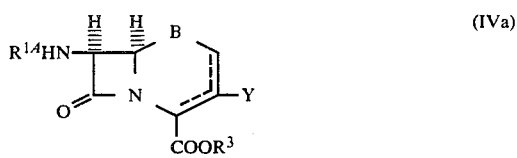

(IVa)

(wherein $R^{14}$, $R^3$, B and the dotted line are as defined above; and Y represents a substituent capable of reacting with one or more reagents to form or introduce a group of formula —CH=CH—C≡C—$R^2$ at the 3-position) with one or more said reagents.

If necessary and/or desired in each instance, where it is desired to form a compound of formula (Ia) as defined above or a non-toxic salt, solvate, 1-oxide or non-toxic metabolically labile ester thereof any of the following steps, in any appropriate sequence, may be carried out:

(i) conversion of a $\Delta^2$-isomer into the desired $\Delta^3$-isomer, (ii) reduction of a compound wherein B is >S→O to form a compound wherein B is >S, (iii) oxidation of a compound wherein B is >S, to form a compound wherein B is >S→O (iv) formation of a non-toxic salt, (v) formation of a solvate, (vi) formation of a non-toxic metabolically labile ester, (vii) separation of isomers, (viii) isomerisation of the double bond in the 3-position side-chain from the cis to the trans configuration, or vice versa, and (ix) removal of any carboxyl blocking and/or O- or N-protecting groups.

Acylating agents which may be employed in process (A) or ($A^1$) for the preparation of compounds of formula (I) or (Ia) include acid halides, particularly acid chlorides or bromides. Such acylating agents may be prepared by reacting a suitable acid, e.g. an acid (III) or a salt thereof with a halogenating agent e.g. phosphorus pentachloride, thionyl chloride or oxalyl chloride.

Acylations employing acid halides may be effected in aqueous and non-aqueous reaction media, conveniently at temperatures of from −50° to +50° C., preferably −40° to +30° C., if desired in the presence of an acid binding agent. Suitable reaction media include aqueous ketones such as aqueous acetone, aqueous alcohols such as aqueous ethanol, esters such as ethyl acetate, halogenated hydrocarbons such as methylene chloride, amides such as dimethylacetamide, nitriles such as acetonitrile, or mixtures of two of more such solvents. Suitable acid binding agents include tertiary amines (e.g. triethylamine or dimethylaniline), inorganic bases (e.g. calcium carbonate or sodium bicarbonate), and oxiranes such as lower 1,2-alkylene oxides (e.g. ethylene oxide or propylene oxide) which bind hydrogen halide liberated in the acylation reaction.

Acids (e.g. acids of formula (III)) may themselves be used as acylating agents in the preparation of compounds of formula (I) or (Ia). Acylations employing acids (III) are desirably conducted in the presence of a condensing agent, for example a carbodiimide such as N,N'-dicyclohexylcarbodiimide or N-ethyl-N'-γ-dimethylaminopropylcarbodiimide; a carbonyl compound such as carbonyldiimidazole; or an isoxazolium salt such as N-ethyl-5-phenylisoxazolium perchlorate.

Acylation may also be effected with other amide-forming derivatives of acids (e.g. acids of formula (III) such as, for example, an activated ester, a symmetrical anhydride or a mixed anhydride (e.g. formed with pivalic acid or with a haloformate, such as a lower alkylhaloformate). Mixed anhydrides may also be formed with phosphorus acids (for example phosphoric or phosphorous acids), sulphuric acid or aliphatic or aromatic sulphonic acids (for example toluene-p-sulphonic acid). An activated ester may conveniently be formed in situ using for example, 1-hydroxybenzotriazole in the presence of a condensing agent as set out above. Alternatively, the activated ester may be preformed.

Acylation reactions involving the free acids or their above-mentioned amide-forming derivatives are desirably effected in an anhydrous reaction medium, e.g. methylene chloride, tetrahydrofuran, dimethylformamide or acetonitrile.

An alternative method of activation is, for example, by reacting an acid (e.g. an acid of formula (III)) with a solution or suspension preformed by adding a carbonyl halide, in particular oxalyl chloride or phosgene, or a phosphoryl halide such as phosphorous oxychloride to a solvent such as a halogenated hydrocarbon, for example methylene chloride, containing a lower acyl tertiary amide such as N,N-dimethylformamide. The activated form of the acid may then be reacted with a 7-amino compound of formula (I) or (II) in a suitable solvent or mixture of solvents for example an alcohol, e.g. aqueous ethanol or aqueous industrial methylated spirits. The acylation reaction may conveniently be effected at temperatures of from −50° to +50° C., preferably −40° to +30° C., if desired in the presence of an acid binding agent, for example as described above (e.g. triethylamine).

If desired, the above acylation reactions may be carried out in the presence of a catalyst such as 4-dimethylaminopyridine.

The acids (e.g. of formula (III)) and acylating agents corresponding thereto may, if desired, be prepared and employed in the form of their acid addition salts. Thus, for example, acid chlorides may conveniently be employed as their hydrochloride salts, and acid bromides as their hydrobromide salts.

Examples of compounds of formula (IV) and (IVa) employed as starting materials in processes (C) and (B¹) above include compounds wherein Y represents a group selected from:

(i) CH=PR$^e$₃ [wherein the groups R$^e$, which may be the same or different, are alkyl, aralkyl, aryl or dialkylamino groups or such a group substituted by one or more halogen atoms, nitro groups, cyano groups, amino groups, substituted amino groups (e.g. alkyl- or acyl-substituted amino groups) or acyl groups] or a Zwitterionic form of the group;

(ii) CH₂Q (where Q represents the group [PR$^e$₃]$^⊕$ (where R$^e$ is as defined above), or the group P(O)R$^f$₂, where the groups R$^f$, which may be the same or different, represent an alkoxy, aryloxy or aralkoxy group, which groups may optionally be substituted by one or more halogen atoms, nitro groups, cyano groups, amino groups, substituted amino groups (e.g. alkyl- or acyl-substituted amino groups) or acyl groups);

(iii) (CH₂)$_n$CHO (where n is zero or 1) or where n is 1, an enol form or derivative (e.g. an acyl derivative) thereof; or (iv) (CH₂)$_n$Z (where n is as defined above and Z represents a readily displaceable atom or group such as a halogen atom, e.g. chlorine or bromine, or an acyloxy group such as trifluoro methanesulphonyloxy, toluene-p-sulphonyloxy, methanesulphonyloxy or acetoxy).

Processes (C) and (B¹) may be carried out in an inert solvent, preferably an inert organic solvent, and conveniently at a temperature of from −80° to +120° C., preferably from 0° to 80° C. Suitable inert organic solvents include, for example, a hydrocarbon, e.g. benzene or toluene; a halogenated hydrocarbon, e.g. dichloromethane; an ether, e.g. diethyl either, tetrahydrofuran or dioxan; an amide, e.g. dimethylformamide, dimethylacetamide or hexamethyl phosphoramide; a sulphoxide, e.g. dimethylsulphoxide; or a sulphone, e.g. sulpholane.

In a particular embodiment of process (B¹), a compound according to the invention may be prepared by reacting a compound of formula (IVa) wherein Y represents the group —CH=PR$^e$₃, or a Zwitterionic form thereof, with a carbonyl compound of the formula

   (V)

wherein R$^{2a}$ is as defined above for R² or a trialkylsilyl group in which the alkyl groups may be the same or different and may be selected from, for example, C₁₋₆ alkyl e.g. methyl.

In this embodiment of the process, the reaction is preferably carried out in a two-phase system containing water and a water immiscible organic solvent, such as a halogenated hydrocarbon, e.g. dichloromethane.

The compounds of formula (IVa) wherein Y represents the group —CH=PR$^e$₃ may be formed in situ from a phosphonium compound of formula —CH₂P-$^⊕$R$^e$₃, by reaction with a base. Suitable bases include, for example, alkali metal and alkaline earth metal hydroxides, carbonates and hydrogen carbonates, e.g. sodium hydroxide or sodium hydrogen carbonate; disodium hydrogen phosphate; hydrides, e.g. sodium hydride; and organic bases such as tertiary nitrogen bases, e.g. triethylamine; or alkyl lithiates, e.g. butyl lithium.

The intermediate formed in the above reaction of a compound of formula (IVa) with a compound of formula (V) in which R$^{2a}$ is a trialkylsilyl group may be converted to a compound in which R² is hydrogen by reaction with, for example, silver nitrate and potassium cyanide.

In a further embodiment of Process (B¹) a compound of formula (IVa) wherein Y represents the group —CH₂Q, or a salt thereof, may be reacted with a carbonyl compound of formula (V) in the presence of a base, to form a compound according to the invention. Suitable bases include those described above.

The compounds of formula (IVa) wherein Y represents the groups —CH=PR$^e$₃ or —CH₂Q may be prepared in conventional manner, for example by the methods described in British Patent Specification No. 1,342,241 or European Patent Application No. 30,630.

According to another embodiment of process (B¹), a compound of the invention may be prepared by reacting a compound of formula (IVa) wherein Y represents the group —$(CH_2)_n$CHO or an enol form or derivative thereof, with a metal salt having an anion of formula $$R^2C\equiv C(CH_2)_m{}^{\ominus} \qquad (VI)$$

(wherein $R^2$ is as defined above, and m is zero when n in the group Y is 1, or is 1 when n is zero).

Examples of metals capable of forming a salt with an anion of formula (VI) include lithium, magnesium, mercury, zinc, cadmium and copper.

When Y represents the group —CHO (i.e. when n is zero), a compound of formula (IVa) may be reacted with a compound of formula $$R^2C\equiv C-CH=PR^e{}_3 \qquad (VII)$$

or a compound of formula $$R^2C\equiv C-CH_2Q \qquad (VIII)$$

(wherein $R^2$, $R^e$ and Q are as defined above), the reaction with a compound of formula (VIII) being carried out in the presence of a base. Suitable bases include alkali metal and alkaline earth metal hydroxides, carbonates and hydrogen carbonates, e.g. sodium hydroxide and sodium hydrogen carbonate; and organic bases such as tertiary nitrogen bases, e.g. triethylamine and alkyl lithiates, e.g. butyl lithium.

If desired, a compound of formula (VII) may be generated by reaction of a corresponding phosphonium compound with a base. Suitable bases include those described above for the reaction of a compound of formula (VIII) with a compound of formula (IVa).

Compounds of formula (IVa) wherein Y represents the group —$(CH_2)_n$CHO may be prepared in conventional manner, for example, by the methods described in British Patent Specification No. 1155024, U.S. Pat. No. 3,351,596 or European Patent Application No. 53962.

According to a still further embodiment of Process (B), a compound of the invention may be prepared by reacting a compound of formula (IVa) wherein Y represents the group —$(CH_2)_nZ$ (wherein n and Z are as defined above) with a metal salt having an anion of formula $$[R^2C\equiv CCHU]^{\ominus} \qquad (IX)$$

[wherein $R^2$ is as defined above and U represents =CH when n in the group Y is zero, or the group $S(O)_wR$ or $Se(O)_wR$ (where w is 1 or 2 and R is an aryl or an aralkyl group) when n in the group Y is 1].

Examples of metals capable of forming a salt with an anion of formula (IX) include those described above.

When U represents =CH, the metal salt having the anion of formula (IX) may be in the form of a metal (e.g. copper) complex, for example LiCu(Ch=CH-.C≡CR²)T, where T may represent the group (CH=CH.C≡CR²) or an organic group capable of forming a complex with copper but which will not participate in the reaction.

Compounds of formula (IVa) wherein Y represents the group —$(CH_2)_nZ$ may be prepared in conventional manner, for example, by the methods described in British Patent Specifications Nos. 1326531 and 1461323.

It will be appreciated that in the above reaction of a compound of formula (IVa) where Y represents a group —$(CH_2)_n$CHO with a metal salt having an anion of formula (VI) an intermediate alcohol may be formed; this may be converted to a compound of the invention with the required carbon-carbon double bond by elimination of water. It may be convenient to convert the intermediate alcohol to an acylated derivative, such as a tosylate, mesylate or acetate and effect an elimination reaction on the acylate so formed. The intermediate which may be formed by reaction of a compound of formula (IVa) wherein Y represents the group —$(CH_2)_nZ$ with a metal salt having an anion of formula (IX), wherein U represents the group $S(O)_wR$ or $Se(O)_wR$ may be converted to a compound of the invention with the required carbon-carbon double bone at the 3-position, by elimination of a sulphenic or sulphinic acid (or the corresponding selenic acid).

Such elimination reactions described above may be effected in a conventional manner, for example, in an inert organic medium, such as that in which the intermediate was formed and at a temperature of from 0° to 100° C. If desired the elimination reaction may be effected in the presence of a catalyst such as a non-nucleophilic base e.g. triethylamine.

The reaction product from the above processes may be separated from the reaction mixture, which may contain, for example, unchanged cephalosporin starting material and other substances, by a variety of processes including recrystallisation, ionophoresis, column chromatography and use of ion-exchangers (for example by chromatography on ion-exchange resins) or macroreticular resins.

A $\Delta^2$-cephalosporin ester derivative obtained in accordance with the process of the invention may be converted into the corresponding desired $\Delta^3$-derivative by, for example, treatment of the $\Delta^2$-ester with a base, such as pyridine or triethylamine.

A ceph-2-em or ceph-3-em reaction product may also be oxidised to yield the corresponding ceph-3-em 1-oxide, for example by reaction with a peracid, e.g. peracetic or m-chloroperbenzoic acid; the resulting sulphoxide may if desired, subsequently be reduced as described hereinafter to yield the corresponding desired ceph-3-em sulphide.

Where a compound is obtained in which B is >S→O this may if desired, be converted into the corresponding sulphide by, for example, reduction of the corresponding acyloxysulphonium or alkoxysulphonium salt prepared in situ by reaction with e.g. acetyl chloride in the case of an acetoxysulphonium salt, reduction being effected by, for example, sodium dithionite or by iodide ion as in a solution of potassium iodide in a water-miscible solvent e.g. acetic acid, acetone, tetrahydrofuran, dioxan, dimethylformamide or dimethylacetamide. The reaction may be effected at a temperature of from −20° to +50° C.

Where any of the above processes produce a mixture of cis and trans geometrical isomers, these may be separated, as desired, by conventional techniques, e.g. by crystallisation, fractional crystallisation or chromatography. Similarly, where the compounds contain an oxime group in the 7-side chain and are obtained as a mixture of syn and anti isomers, the syn isomer may be obtained by such conventional methods.

In order to facilitate the separation of the cis and trans isomers, it may be convenient to oxidise the mixture of cephalosporin cis and trans isomers to the corresponding sulphoxides, separate the cis and trans isomers by the methods described above and, if desired, reduce the sulphoxides to the required sulphides, for example by the methods herein described.

If necessary and/or desired, the cis isomer may be isomerised to the corresponding trans isomer, for example, by heating a mixture of the cis and trans isomers in an inert solvent such as toluene at a temperature of, for example, from 80° to 110° C.

In some cases, for example, when no oxime substituent is present, the reaction mixture may advantageously contain an isomerisation catalyst, such as iodine.

Metabolically labile ester derivatives of the compounds of formula (Ia) may be prepared by reacting the compound of formula (Ia) or a salt or protected derivative thereof with the appropriate esterifying agent such as an acyloxyalkyl halide (e.g. iodide) conveniently in an inert organic solvent such as dimethylformamide or acetone, followed, where necessary, by removal of any protecting groups.

Base salts of the compounds of formula (I) or (Ia) may be formed by reacting the acid of formula (I) or (Ia) with an appropriate base. Thus, for example, sodium or potassium salts may be prepared using the respective 2-ethylhexanoate or hydrogen carbonate salt. Acid addition salts may be prepared by reacting a compound of formula (I) or (Ia) or a metabolically labile ester derivative thereof with the appropriate acid.

Compounds of formula (II) (i.e. compounds of formula (I) wherein R represents an amino group) used as starting materials in processes (A), (B) and (A$^1$) may generally be prepared by N-deacylating a compound of formula (I) wherein R represents an acylated amino group in which the acyl group may be removed under suitable conditions. In particular, the said starting materials may be prepared by N-deacylating compound of formula(X)

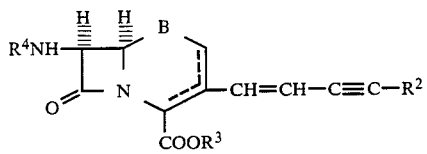

(wherein $R^2$, $R^3$, B and the dotted line are as defined above, and $R^4$ represents a carboxylic acyl group selected from e.g. formyl, phenoxyacetyl, phenylacetyl, substituted phenoxy- or phenylacetyl, thienylacetyl, or 5-amino-adipoyl, or the latter having one or both of the carboxyl and amino groups thereof blocked; or t-butoxycarbonyl or such carbonic acyl group; or the group $R^4$ and the adjacent hydrogen atom together represent a diacyl grouping derived from a diacarboxylic acid, e.g. a phthalimido or maleimido group, $R^4NH$ thus being an N-attached heterocyclic group. The compounds of formula (X) may themselves be prepared by methods analogous to process (C) above. The N-deacylation may be effected in conventional manner, e.g. using PCl$_5$ as described in British Patent Specification No. 1241655.

Alternatively the compound of formula (II) may be prepared from a 7-amino cephalosporin compound by methods analogous to process (C) above.

Acids of formula (III) may be prepared by conventional techniques.

For use as starting materials for the preparation of compounds according to the invention in which the 7-side chain contains an oxime group, compounds of general formula (III) and acid halides and anhydrides corresponding thereto, as well as compounds of formula (IVa) are preferably used in their syn isomeric form or in the form of mixtures of the syn isomers and the corresponding anti isomers containing at least 90% of the syn isomer.

It should be appreciated that in some of the above transformations it may be necessary to protect any sensitive groups in the compound in question to avoid undesirable side reactions. Suitable protecting group are described in, e.g. "Protective Groups in Organic Chemistry" by J. F. W. McOmie (Plenum Press, London, 1973) and "Protective Groups in Organic Synthesis" by Theodora W. Greene (Wiley Interscience, New York, 1981). For example, during any of the reaction sequences referred to above it may be necessary to protect any NH$_2$ group e.g. in an aminothiazolyl moiety, for example by tritylation, acylation (e.g. chloroacetylation of formylation), protonation or other conventional method. The protecting group may thereafter be removed in any convenient way which does not cause breakdown of the desired compound, e.g. in the case of a trityl group by using an optionally halogenated carboxylic acid, e.g. acetic acid, formic acid, chloroacetic acid or trifluoroacetic acid or using a mineral acid, e.g. hydrochloric acid or mixtures of such acids, preferably in the presence of a protic solvent such as water, or, in the case of a chloroacetyl group, by treatment with thiourea.

Carboxyl blocking or hydroxyl protecting groups used in the preparation of compounds of the invention or in the preparation of necessary starting materials are or desirably groups which may readily be split off at a suitable stage in the reaction sequence, conveniently at the last stage. It may, however, be convenient in some instances to employ non-toxic metabolically labile carboxyl blocking groups such as acyloxymethyl or -ethyl groups (e.g. acetoxymethyl or -ethyl or pivaloyloxymethyl) and retain these in the final product to give an appropriate ester derivative of the compound of formula (Ia).

Suitable carboxyl blocking and hydroxyl protecting groups are well known in the art, a list of representative blocked carboxyl groups being included in British Pat. No. 1399086. Preferred blocked carboxyl groups include aryl lower alkoxycarbonyl groups such as p-methoxybenzyloxycarbonyl, p-nitrobenzyloxycarbonyl and diphenylmethoxycarbonyl; lower alkoxycarbonyl groups such as t-butoxycarbonyl; and lower haloalkoxycarbonyl groups such as 2,2,2-trichloroethoxycarbonyl. Representative hydroxyl protecting groups include alkyl, aralkyl, aryl and acyl groups. The blocking and/or protecting groups may subsequently be removed by any of the appropriate methods disclosed in the literature; thus, for example, acid or base catalysed hydrolysis is applicable in many cases, as are enzymically-catalysed hydrolyses.

The antibiotic compounds of the invention may be formulated for administration in any convenient way, by analogy with other antibiotics and the invention therefore includes within its scope pharmaceutical compositions comprising an antibiotic compound in accordance with the invention adapted for use in human or veterinary medicine. Such compositions may be presented for use in conventional manner with the aid of any necessary pharmaceutical carriers or excipients.

The compositions may be presented in a form suitable for absorption by the gastro-intestinal tract, especially where the active ingredient exhibits oral absorption, such as the above-mentioned particularly preferred trans isomer. Tablets and capsules for oral administration may be in unit dose presentation form, and may contain conventional excipients such as binding agents, for example, syrup, acacia, gelatin, sorbitol, tragacanth, or polyvinylpyrrolidone; fillers, for example, lactose, sugar, maize-starch, calcium phosphate, sorbitol or glycine; tabletting lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspensions, solutions, emulsions, syrups, or elixirs or may be presented as a dry product, for reconstitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel of hydrogenated edible fats; emulsifying agents, for example, lecithin, sorbitan mono-oleate or acacia; non-aqueous vehicles which may include edible oils, for example, almond oil, fractionated coconut oil, oily esters, propylene glycol, or ethyl alcohol; preservatives, for example, methyl or propyl p-hydroxybenzoates or sorbic acid. Suppositories will contain conventional suppository bases, e.g. cocoa butter or other glycerides.

The antibiotic compounds according to the invention may also be formulated for injection and may be presented in unit dose form, in ampoules, or in multi-dose containers, if necessary with an added preservative. The compositions may also take such forms as suspensions, solutions, or emulsions in oily or aqueous vehicles, and may contain formulatory agents such as suspending, stabilising and/or dispersing agents. Alternatively the active ingredient may be in powder form for reconstitution with a suitable vehicle, e.g. sterile, pyrogen-free water, before use.

If desired, such powder formulations may contain an appropriate non-toxic base in order to improve the water-solubility of the active ingredient and/or to ensure that when the powder is reconstituted with water, the pH of the resulting aqueous formulation is physiologically acceptable. Alternatively the base may be present in the water with which the powder is reconstituted. The base may be, for example, an inorganic base such as sodium carbonate, sodium bicarbonate or sodium acetate, or an organic base such as lysine or lysine acetate.

Compositions for veterinary medicine may, for example, be formulated as intramammary preparations in either long acting or quick-release bases.

The compositions may contain from 0.1% upwards, e.g. 0.1–99% of the active material, depending on the method of administration. When the compositions comprise dosage units, each unit will preferably contain 50–3000 mg e.g. 100 to 2000 mg of the active ingredient. The dosage as employed for adult human treatment will preferably range from 200 to 12000 mg e.g. 500–6000 mg per day, depending on the route and frequency of administration, the nature of the infection and the activity of the antibiotic against the infecting organism. For example, in adult human treatment 500 to 4000 mg per day administered intravenously or intramuscularly will normally suffice. For oral administration to adult humans the daily dose will range from 200 to 4000 mg per day, e.g. 500 to 2000 mg per day and for children it will range for example, from 125 to 1000 mg per day.

The invention further provides a method of combating bacterial infections in human and animal subjects wherein an antibacterially effective amount of an antibiotic compound of formula Ia as defined above or a non-toxic salt or non-toxic metabolically labile ester thereof is administered prophylactically or therapeutically to said subject.

The invention additionally provides the use of a compound of formula Ia as defined above or a non-toxic salt or non-toxic metabolically labile ester thereof for manufacturing a pharmaceutical or veterinary composition for use in combating bacterial infections in humans and animals.

The antibiotic compounds according to the invention may be administered in combination with other therapeutic agents such as antibiotics, for example penicillins or other cephalosporins.

The following Examples serve to illustrate the invention. All temperatures are in °C.

PREPARATION 1

[(6R,7R)-7-[(Z)-2-(t-Butoxycarbonylmethoxyimino)-2-(2-tritylaminothiazol-4-yl)acetamido]-4-diphenylmethoxycarbonylceph-3-em-3-ylmethyl]triphenylphosphonium bromide A solution of triphenylphosphine (0.524 g) and diphenylmethyl (6R,7R)-3-bromomethyl-7-[(Z)-2-(t-butoxycarbonylmethoxyimino)-2-(2-tritylaminothiazol-4-yl)acetamido]ceph-3-em-4-carboxylate (0.985 g) [prepared according to the method of UK Patent Specification No. 2036738A] in ethyl acetate (10 ml) was stirred at ambient temperature for 16 hr. During this time, a solid was deposited. This was filtered off, washed with ethyl acetate, and dried in vacuo to give the title compound (0.848 g); $\nu_{max}$ (CHBr$_3$) 3385, 3280 (NH), 1790 ($\beta$-lactam), 1728, 1720 (ester), 1680, 1522 cm$^{-1}$ (amide).

Preparation 2

(Z)-2-(2-Diphenylmethoxycarbonylmethoxyimino)-2-(2-tritylaminothiazol-4-yl)acetic acid A stirred solution of (Z)-2-(hydroxyimino)-2-(2-tritylaminothiazol-4-yl)acetic acid, sodium salt in DMF (50 ml) was treated with potassium t-butoxide (1.0 g) under nitrogen, at 0°. After 40 mins the solution was cooled to −40° and treated with more potassium t-butoxide (1.0 g). When the base had completely dissolved a solution of diphenylmethyl bromoacetate (4.7 g) in DMF (10 ml) was added dropwise. After 40 mins the reaction mixture was allowed to warm to −20°. After a further 30 mins 2N hydrochloric acid (15 ml) was added and the mixture was partitioned between ethyl acetate (100 ml) and water (100 ml). Work up of the organic phase followed by evaporation of the solvent gave a foam which was crystallised from ethyl acetate-petrol to give title compound as a solid (2.07 g); $\tau$(CDCl$_3$) values include 3.11 (—CO$_2$CH), 3.28 (thiazole.5H), 5.34 (—OCH$_2$CO$_2$—).

PREPARATION 3

Diphenylmethyl(6R,7R)-3-bromomethyl-7-[(Z)-2-(diphenylmethoxycarbonylmethoxyimino)-2-(2-tritylaminothiazol-4-yl)acetamido]ceph-3-em-4-carboxylate A solution of oxalyl chloride (3.19 ml) in dichloromethane (40 ml) was added dropwise to a stirred solution of DMF (3.87 ml) in dichloromethane (160 ml) at −15°, under nitrogen. The resulting white suspension was maintained at ca −5° for 30 mins and then cooled to −10°. The product of Preparation 2 (21.77 g) was added and the resulting orange solution was stirred at between −5° and 0° for 30 mins before being recooled to −10°.

Meanwhile, a stirred suspension of diphenylmetnyl (6R,7R)-bromomethyl-7-amino-ceph-3-em-4-carboxylate hydrochloride salt (16.51 g) in dichloromethane (200 ml) was treated with triethylamine (4.64 ml) and N,N-dimethylaniline (9.51 ml) at −25° After a few minutes the solution of activated side-chain acid was added and the reaction mixture was allowed to warm to 5° over 90 mins. The mixture was poured into water (500 ml) and the two phases were separated. The organic phase was washed with 2N hydrochloric acid (2×500 ml), water (500 ml), saturated sodium bicarbonate solution (500 ml) and brine (500 ml) and dried (magnesium sulphate). The solvent was removed and the residue was purified by chromatography to give the title compound as a foam (29.23 g). $\tau$(CDCl$_3$) values include 2.08 (—CONH), 4.11 (7H), 4.96, 5.11 (—OCH$_2$CO$_2$—), 4.99 (6H), 5.54, 5.83 (—CH$_2$Br).

PREPARATION 4

(6R,7R)-7-[(Z)-2-(Diphenylmethoxycarbonylmethoxyimino)-2-(2-tritylaminothiazol-4-yl)acetamido]-4-diphenylmethoxycarbonyl-ceph-3-em-3-ylmethyl)triphenylphosphonium bromide The title compound was prepared from diphenylmethyl (6R,7R)-3-bromomethyl-7-[(Z)-2-(diphenylmethoxycarbonylmethoxyimino)-2-(2-tritylaminothiazol-4-yl)acetamido]ceph-3-em-4-carboxylate according to the method of Preparation 1 and exhibited $\tau$(CDCl$_3$) values include 4.18 (7H), 4.94 (6H), 3.92, 4.87 (—CH$_2$P) and 5.00 (—CH$_2$CO$_2$—).

PREPARATION 5

Diphenylmethyl(6R,7R)-7-Formamido-3-[(E)- and (Z)-pent-1-en-3-ynyl]ceph-3-em-4-carboxylate A stirred solution of (6R,7R)-[4-diphenylmethoxycarbonyl-7-formamidoceph-3-em-ylmethyl]triphenylphosphonium bromide (7.61 g) in dichloromethane (100 ml) was treated with saturated sodium bicarbonate solution (60 ml). After 5 minutes but-2-ynal (1.38 g) was added and the mixture stirred for 3 hours. The phases were separated and the organic phase was washed with water, 2M hydrochloric acid, water and brine, (200 ml of each), dried (sodium sulphate), and evaporated. The residue was purified by column chromatography (200 g silica gel), eluting with ethyl acetate:dichloromethane (1:9) to give a mixture of the title compounds as a solid (2.18 g); (E):(Z) 1:3, $\lambda_{max}$ (ethanol) 258.5 nm ($\epsilon$4,600), 265.5 nm ($\epsilon$4,600), 325 nm ($\epsilon$17,500); $\nu_{max}$ (CHBr$_3$) 3415 (NH), 2210 (C≡C), 1786 ($\beta$-lactam), 1722 (CO$_2$R), 1700, 1500 cm$^{-1}$ (HCONH); $\tau$(DMSO-d6) 3.42, 4.30 (CH=CH—C≡C—, Z isomer), 3.87 (—CH=CH—C≡C, E isomer), 5.70, 6.07 (2-CH$_2$, Z isomer), 6.06, 6.35 (2-CH$_2$, E isomer), 7.97 (—C≡C—CH$_3$).

PREPARATION 6

Diphenylmethyl(6R,7R)-7-Formamido-3-[(E)-pent-1-en-3-ynyl]ceph-3-em-4-carboxylate A solution of the product of Preparation 5 (2.11 g) in toluene (100 ml) containing a crystal of iodine was heated at reflux for 5 hours, under nitrogen On cooling the precipitated solid was filtered off, washed with toluene and ether and dried to give the title compound as fine needles (794 mg). (The mother liquors were reprocessed and chromatographed to afford further material (796 mg)). The title compound exhibited $\lambda_{max}$ (ethanol) 328 nm ($\epsilon$26,100); $\nu_{max}$ (CHBr$_3$) 3415, 3340 (NH), 2215 (C≡C)—, 1786 ($\beta$-lactam), 1725 (CO$_2$R), 1698, 1500 cm$^{-1}$ (CONH); $\tau$(CDCl$_3$) 1.80 (CHO), 3.02 (CHPh$_2$), 3.44 (NH), 4.13 (7H), 4.20 (—CH=CH—C≡C), 5.03 (6H), 6.45 and 6.56 (2-CH$_2$), 8.01 (CH$_3$).

PREPARATION 7

Diphenylmethyl(6R,7R)-7-Amino-3-[(E)-pent-1-en-3-ynyl]ceph-3-em-4-carboxylate, Hydrochloride A stirred solution of the product of Preparation 6 (710 mg) in methanol (5 ml) and ether (5 ml) was treated dropwise with phosphorus oxychloride (0.29 ml) at 0°. The reaction mixture was allowed to warm to 20° over 90 minutes and the resulting solution was concentrated to 2 ml by evaporation and added to ether (50 ml) to give the title hydrochloride as a solid (534 mg); $\lambda_{max}$ (ethanol) 270 nm ($\epsilon$4800), 328 nm ($\epsilon$22,600); $\nu_{max}$ (Nujol) 2600 (NH$_3$), 2210 (C≡C), 1782 ($\beta$-lactam), 1718 cm$^{-1}$ (CO$_2$R); $\tau$(DMSO-d6) 2.92 (—CH=CH—C≡C), 3.74 (CH=CH—C≡C), 5.99, 6.26, (2̄-CH$_2$), and 7.97 (C≡C—CH$_3$).

PREPARATION 8

Diphenylmethyl(6R,7R)-7-Amino-3-[(E)-pent-1-en-3-ynyl]ceph-3-em-4-carboxylate

A solution of Preparation 7 (10 g) in dichloromethane (100 ml) was shaken for 5 mins with sodium bicarbonate solution (100 ml). Work up of the organic phase gave the title compound as a foam (942 mg); $\tau$(CDCl$_3$) values include 2.84 (—CH=CH—C≡C), 4.24 (—CH=CH—C≡C), 5.05 (7H), 5.26 (6H), 8.03 (C≡C—CH$_3$).

PREPARATION 9

Dimethyl(1,1-dimethylethyl)(2-propynyloxy)silane

A solution of propargyl alcohol (8.7 ml), t-butyldimethyl silyl chloride (25. g) and 4-dimethylaminopyridine (0.73 g) in methylene chloride (45 ml) was cooled to 0°. Triethylamine (25.1 ml) was added dropwise over 5 mins with stirring. After 18 h the mixture was diluted with methylene chloride (50 ml) and extracted with water (2×75 ml). The aqueous solutions were combined and then extracted with methylene chloride (25 ml). The organic phases were combined and washed with water and saturated aqueous ammonium chloride, dried and evaporated to give an oil (24.9 g). Distillation under reduced pressure afforded the title compound as an oil (20.8 g); bp 60°–62° (24 mm Hg).

PREPARATION 10

4-[Dimethyl(1,1-dimethylethyl)silyloxy]-2-butynoic acid

A solution of 1.6M butyl lithium in hexane (18.3 ml) was cooled to −50° and THF (25 ml) was added. The product of Preparation 9 (5.0 g) in THF (5 ml) was added dropwise with stirring under nitrogen, keeping the reaction temperature below −50°. When the addition of the acetylene was complete, (ca 10 mins), the flow of nitrogen was stopped and dry carbon dioxide bubbled through the vigorously stirred suspension while maintaining its temperature below −50°. After 2 h the cooling bath was removed and the mixture allowed to warm to room temperature. Introduction of the carbon dioxide was continued for a further 0.5 h.

The suspension was slowly poured onto a solution of ammonium chloride (3.5 g) in water (12 ml) and then a mixture of concentrated hydrochloric acid (3 ml) and water (3 ml) added with gentle swirling. The aqueous phase was separated off and extracted with THF (4×50 ml). The organic extracts were combined, dried, and evaporated to give the title compound as a low melting solid (6.6 g) $\tau$(CDCl$_3$) values include 5.50 (C≡C—CH$_2$), 9.82 (C(CH$_3$)$_3$).

PREPARATION 11

4-[Dimethyl(1,1-dimethylethyl)silyloxy]-2-butynoic acid ethyl ester

To a cooled ($-5°$)solution of 1.6M butyl lithium in n-hexane (62.4 ml) and ether (50 ml) was added the product of Preparation 9 (17.0 g) in ether (50 ml) with stirring under nitrogen. A solution of ethyl chloroformate (13.3 ml) in ether (10 ml) was added in one portion to the cooled ($-78°$) reaction mixture. The mixture was allowed to warm to room temperature over 4 h and then poured onto ice. The layers were swirled and the upper layer immediately separated off. The lower, aqueous layer was extracted with ether (3×100 ml). The organic extracts were combined, dried, and evaporated to give an oil (26.25 g). This was distilled under reduced pressure to give the title ester bp 86.88°/0.2 mm Hg as an oil.

PREPARATION 12

4-[Dimethyl(1,1-dimethylethyl)silyloxy]-2-butynoic acid, diphenylmethylester

A solution of 0.5M diphenyldiazomethane in methylene chloride (59 ml, 30 m.mol) was added dropwise to a cooled (5°) stirred solution of the product of Preparation 10 (6.3 g) in dichloromethane (100 ml) over 1 h. The reaction mixture was allowed to warm to room temperature over 17 h and was then evaporated to a purple gum. This gum was taken into methylene chloride (100 ml) and formic acid added dropwise until the purple colour had been discharged. The resulting solution was evaporated to an oil (11.4 g) which was purified by chromatography to give the title compound as an oil (3.00 g). $\tau$(CDCl$_3$) values include 3.04 (—CO$_2$CH—), 5.52 (C≡C—CH$_2$).

PREPARATION 13

4-Hydroxy-2-butynoic acid, diphenylmethyl ester

To a solution of the product of Preparation 12 in acetonitrile (50 ml) was added 40% aqueous hydrofluoric acid (1 ml) with stirring at room temperature. After 1 h the reaction mixture was partitioned between chloroform and water. Work up of the organic phase followed by evaporation gave a viscous brown oil (2.9 g) which was purified by chromatography to give the title compound as a viscous oil $\tau$(CDCl$_3$) values include 3.06 (—CO$_2$CH—), 5.63 (C≡C—CH$_2$—), 7.76 (OH).

PREPARATION 14

4-Oxo-2-butynoic acid, diphenyl ester

The product of Preparation 13 (2.80 g) in ether (280 ml) was treated with 'very active' manganese dioxide (28 g) added portion wise with stirring at room temperature. After 1 h the suspension was filtered and the filtrate evaporated to an oil (1.15 g) $\tau$(CDCl$_3$) values are 0.67 (—CHO), 2.67 (Ph), 3.01 (CO$_2$CH—).

PREPARATION 15

4-Hydroxy-2-butynoic acid, ethyl ester

The title compound was prepared as an oil according to the method of Preparation 13 from the product of Preparation 11 (6.50 g) and exhibited $\tau$(CDCl$_3$) values include 5.58 (C≡C—CH$_2$—), 5.76 (CO$_2$.CH$_2$), 8.72 (CO$_2$CH$_2$CH$_3$).

PREPARATION 16

4-Oxo-2-butynoic acid, ethyl ester

The title compound (0.74 g) was prepared as an oil from the product of Preparation 15 (1.99 g) according to the method of Preparation 14 and exhibited $\tau$(CDCl$_3$) values of 0.77 (CHO), 5.74 (—CO$_2$CH$_2$—), 8.67 (CO$_2$CH$_2$CH$_3$).

PREPARATION 17

Diphenylmethyl(6R,7R)-Formamido-3-[(E)- and (Z)-pent-1-en-3-ynyl]ceph-3-em-4-carboxylate To a solution of (6R,7R)-[4-diphenylmethoxycarbonyl-7-formamidoceph-3-em-3-ylmethyl]triphenyl phosphonium bromide (56.5 g) in dichloromethane (700 ml) was added saturated aqueous sodium bicarbonate (450 ml) with vigorous stirring at 21° for 5 min. But-2-ynal was added and the 2 phase mixture stirred at 21° for 1 hour and allowed to stand at 10° for 15 hours. The phase were separated, and the aqueous phase extracted with dichloromethane (2×200 ml). The combined organic phases were washed sequentially with water (500 ml), 2M aqueous HCl (500 ml), water (500 ml) and saturated brine (500 ml), and dried over magnesium sulphate. Removal of the solvent in vacuo gave a foam, which was chromatographed on Merck Kieselgel 60 (230–400 mesh) (1.3 kg), and eluted sequentially with ethyl acetate:dichloromethane (1:9) and (1:5) respectively. Appropriate fractions were combined to give the title compounds as a solid (13.80 g); (E):(Z) 1:4 by $^1$H n.m.r.; $\lambda_{max}$ (ethanol) 264.5 nm ($\epsilon$5 000) and 323 nm ($\epsilon$18 000); $\nu_{max}$ (CHBr$_3$) and $\tau$(DMSO-d$_6$) values similar to Preparation 5.

PREPARATION 18

Diphenylmethyl(6R,7R)-7-Formamido-3-[(E)-pent-1-en-3-ynyl]ceph-3-em-4-carboxylate A 1:4 mixture (by $^1$H n.m.r.) of diphenylmethyl(6R,7R)-7-formamido-3-[(E)- and (Z)-pent-1-en-3-ynyl]ceph-3-em-4-carboxylate (13.75 g) was suspended in toluene (600 ml), a few crystals of iodine added, and the mixture heated under reflux for 5 hours, under nitrogen. Further crystals of iodine were added after every hour. The reaction mixture was cooled in ice and a seed crystal of the title compound added. The resultant precipitate was filtered off, washed sequentially with cold toluene (2×30 ml) and ether (2×30 ml) and dried to give a solid (6.87 g) which was recrystallised from methanol (500 ml) to give the title compound as fine needles (4.56 g); $[\alpha]_D^{21} -125°$ (c 0.53 in CHCl$_3$); $\nu_{max}$ (ethanol) 327 nm ($\epsilon$26, 600); $\nu_{max}$ (CHBr$_3$) and $\tau$(CDCl$_3$) values similar to Preparation 6. The methanol mother liquor was concentrated to a residue which was combined with the toluene mother liquor and the mixture concentrated to 300 ml. The above procedure was repeated four times to afford a total of (4.80 g) of the title compound as fine needles.

EXAMPLE 1

(a)

Diphenylmethyl(6R,7R)-7-[(Z)-2-(t-butoxycarbonyl-methoxyimino)-2-(2-tritylaminothiazol-4-yl)acetamido]-3-[(E & Z)-pent-1-en-3-ynyl)]ceph-3-em-4-carboxylate A stirred solution of the product of Preparation 1 (1.0 g) in dichloromethane (15 ml) was treated with saturated sodium bicarbonate solution (5 ml). After a few minutes but-2-yn-1-al (prepared according to the method of S. Galaj and Y-L. Pascal, Bull. Soc. Chim. France, 3979 (1972)) (0.29 ml) was added and the mixture was stirred for 3.25 hours. Water (10 ml) and dichloromethane (25 ml) were added and the two phases were separated. The organic phase was washed with 2M hydrochloric acid (50 ml), water (50 ml) and saturated sodium chloride solution (50 ml), dried over sodium sulphate, and evaporated. The residue was purified on a column of silica gel (40 g), eluting with a mixture of ethyl acetate and dichloromethane (1:19) to give a mixture of the title compounds as a foam (0.482 g); $\nu_{max}$ (CHBr$_3$) 3380 (NH), 3260 (NH), 2210 (—C≡C—) 1788 ($\beta$-lactam), 1680, 1524 cm$^{-1}$ (—CONH—); $\tau$(DMSO-d6) 1.40 (—CONH, E isomer), 1.42 (—CONH, Z isomer, 3.18 (—CO$_2$CHPh$_2$, Z isomer), 3.20 (—CO$_2$CHPh$_2$, E isomer), 3.28 (—CH=CH—C≡C—CH$_3$, Z isomer), 4.13 (7H), 4.24 (—CH=CH—C≡C—CH$_3$, E isomer), 4.45 (—CH=CH—C≡C—CH$_3$, Z isomer), 4.93 (6H, Z isomer), 4.94 (6H, E isomer), 5.25 (—OCH$_2$CO$_2$—), 5.77, 6.16 (2-CH$_2$, Z isomer), 6.48, 6.59 (2-CH$_2$, E isomer), 8.02 (—C≡C—CH$_3$).

(b)

Diphenylmethyl(1S,6R,7R)-7-[(Z)-2-(t-butoxycarbonylmethoxyimino)-2-(2-tritylaminothiazol-4-yl)acetamido]-3-[(E)-pent-1-en-3-ynyl]ceph-3-em-4-carboxylate, 1-oxide and diphenylmethyl(1S,6R,7R)-7-[(Z)-2-(t-butoxycarbonylmethoxyimino)-2-(2-tritylaminothiazol-4-yl)acetamido]-3-[(Z)-pent-1-en-3-ynyl]ceph-3-em-4-carboxylate, 1-oxide 85% m-Chloroperbenzoic acid (0.325 g) was added to a stirred solution of the product of stage (a) (1.53 g) in dichloromethane (40 ml) at −20°. The mixture was stirred at −20° for 15 minutes before being allowed to warm to 0° over 45 minutes. The mixture was diluted with dichloromethane (35 ml), washed with saturated sodium bicarbonate solution (2×75 ml), saturated sodium chloride (75 ml), dried over sodium sulphate and evaporated. The residue was purified by medium pressure chromatography on a column of silica gel (500 g). Elution with a mixture of chloroform and ether (9:1) gave diphenylmethyl(1S,6R,7R)-7-[(Z)-2-(t-butoxycarbonylmethoxyimino)-2-(2-tritylaminothiazol-4-yl)acetamido]-2-[(Z)-pent-1-en-3-ynyl]ceph-3-em-4-carboxylate, 1-oxide as a foam (0.665 g); $\lambda_{max}$ (ethanol) 321.5 nm ($\epsilon$19500); $\nu_{max}$ (CHBr$_3$) 3380 (NH), 2200 (—C≡C—), 1802 ($\beta$-lactam), 1728 (CO$_2$R), 1678, 1520 (—CONH—), 1048 cm$^{-1}$ (S=O); $\tau$(CDCl$_3$) 3.11 (—CH=CH—C≡C—CH$_3$), 4.45 (—CH=CH—C≡C—CH$_3$), 5.26, 6.56 (2-CH$_2$). Further elution, with the same eluant, gave diphenylmethyl(1S,6R,7R)-7-[(Z)-(t-butoxycarbonylmethoxyimino)-2-(2-tritylaminothiazol-4-yl)acetamido]-3-[(E)-pent-1-en-3-ynyl]ceph-3-em-4-carboxylate, 1-oxide as a foam (0.366 g); $\lambda_{max}$ (ethanol) 328 nm ($\epsilon$26900); $\nu_{max}$ (CHBr$_3$) 3380 (NH), 2215 (—C≡C—), 1800 ($\beta$-lactam), 1726 (—CO$_2$R), 1678, 1520 (—CONH—), 1062 cm$^{-1}$ (S=O); $\tau$(CDCl$_3$) 4.26 (—CH=CH—C≡C—CH$_3$), 6.11, 6.91 (2-CH$_2$).

(c)

Diphenylmethyl(6R,7R)-7-[(Z)-2-(t-butoxycarbonylmethoxyimino)-2-(2-tritylaminothiazol-4-yl)acetamido]-3-[(E)-pent-1-en-3-ynyl]ceph-3-em-4-carboxylate Potassium iodide (581 mg) was added to a stirred solution of diphenylmethyl(1S,6R,7R)-[(Z)-2-(t-butoxycarbonylmethoxyimino)-2-(2-tritylaminothiazol-4-yl)acetamido]-3-[(E)-pent-1-en-3-ynyl]ceph-3-em-4-carboxylate, 1-oxide (425 mg) in dimethylformamide (10 ml) at −20°. After a few minutes acetyl chloride (0.124 ml) was added and the mixture allowed to warm to 0° over 30 mins. After stirring for a further 1.25 hours at 0° the mixture was added to vigorously stirred 10% sodium metabisulphite solution (40 ml) and extracted with ethyl acetate (2×40 ml). The combined extracts were washed with water (2×40 ml) and saturated sodium chloride solution (40 ml), dried over sodium sulphate and evaporated. The residue was purified on a column of silica gel (15 g) eluting with a mixture of ethyl acetate and dichloromethane (1:19) to give the title compound as a foam (331 mg); $\lambda_{max}$ (ethanol); 322.5 nm ($\epsilon$24600); $\nu_{max}$ (CHBr$_3$) 3390, 3260 (NH), 2210 (—C≡C—), 1788 ($\beta$-lactam), 1728 (CO$_2$R), 1680, 1524 cm$^{-1}$ (—CONH—); $\tau$(CDCl$_3$) 4.23 (—CH=CH—C≡C—Ch$_3$), 6.46, 6,56 (2-CH$_2$).

(d)

Diphenylmethyl(6R,7R)-7-[(Z)-2-(t-butoxycarbonylmethoxyimino)-2-(tritylaminothiazol-4-yl)acetamido]-3-[(Z)-pent-1-en-3-ynyl]-ceph-3-em-4-carboxylate Potassium iodide (1.086 g) was added to a stirred solution of diphenylmethyl(1S,6R,7R)-7-[(Z)-2-(t-butoxycarbonylmethoxyimino)-2-(2-tritylaminothiazol-4-yl)acetamido]-3-[(Z)-pent-1-en-3-ynyl]ceph-3-em-4-carboxylate, 1-oxide (795 mg) in dimethylformamide (15 ml) at −20°. After a few minutes acetyl chloride (0.23 ml) was added and the mixture allowed to warm to 0° over 30 mins. After stirring for a further 30 mins at 0° the mixture was added to vigorously stirred 10% sodium metabisulphite solution (75 ml) and extracted with ethyl acetate (75 ml). The combined extracts were washed with water (2×75 ml) and saturated sodium chloride solution (75 ml), dried over sodium sulphate and evaporated. The residue was purified on a column of silica gel (25 g), eluting with a mixture of ethyl acetate and dichloromethane (1:19) to give the title compound as a foam (625 mg); $\lambda_{max}$ (ethanol), 318 nm ($\epsilon$21000); $\nu_{max}$ (CHBr$_3$) 3390, 3260 (NH), 1790 ($\beta$-lactam), 1728 (CO$_2$R), 1682, 1524 cm$^{-1}$ (—CONH—); $\tau$(CDCl$_3$) 1.42 (—CONH), 3.08 (—CO$_2$CHPh$_2$), 3.17 (thiazolyl), 3.28 (—CH=CHC≡C—CH$_3$), 4.13 (7H), 4.45 (—CH=CH—C≡C—CH$_3$), 4.93 (6H), 5.24 (—OCH$_2$CO$_2$—), 5.76, 6.16 (2-CH$_2$), 8.02 (—C≡C—CH$_3$).

(e)

(6R,7R)-7-[(Z)-2-(2-Aminothiazol-4-yl)-2-(carboxymethoxyimino)acetamido]-3-[(E)-pent-1-en-3-ynyl]-ceph-3-em-4-carboxylic acid, trifluoroacetate salt Diphenylmethyl(6R,7R)-7-[(Z)-2-(t-butoxycarbonylmethoxyimino-2-(2-tritylaminothiazol-4-yl)acetamido]-

3-[(E)-pent-1-en-3-ynyl]ceph-3-em-4-carboxylate (295 mg) was stirred with trifluoroacetic acid (4 ml) and anisole (1 ml) for 1 hour. The solution was added dropwise to vigorously stirred water (50 ml). Ether (50 ml) was added and after a few minutes the two phases were separated and the organic phase extracted with water (10 ml). The combined aqueous extracts were washed with ether (3×25 ml), back-washing each time with water (5 ml), concentrated and freeze-dried to give the title compound as a foam (137 mg); $\lambda_{max}$ (ethanol) 233 nm ($\epsilon$19900), 317.5 nm ($\epsilon$24700); $\nu_{max}$ (Nujol) 3300 (NH), 2210 (—C≡C—), 1772 ($\beta$-lactam), 2600, 1720 (—CO$_2$H) 1670, 1560 (—CONH—), 1670 cm$^{-1}$ (CF$_3$CO$_2$—); $\tau$(DMSO-d6) 0.46 (—CONH), 2.93 (CH═CH—C≡C—CH$_3$), 3.15 (thiazolyl), 3.94 (CH═CH—C≡C—CH$_3$), 4.17 (7H), 4.77 (6H), 5.38 (—OCH$_2$CO$_2$—), 6.16, 6.41 (2-CH$_2$), 7.99 (—C≡C—CH$_3$).

(f)

(6R,7R)-7-[(Z)-2-(2-Aminothiazol-4-yl)-2-(carboxymethoxyimino)acetamido]-3-[(Z)-pent-1-en-3-ynyl]ceph-3-em-4-carboxylic acid, trifluoroacetate salt Diphenylmethyl(6R,7R)-7-[(Z)-2-(t-butoxycarbonylmethoxyimino)-2-(2-tritylaminothiazol-4-yl)acetamido]-3-[(Z)-pent-1-en-3-ynyl]ceph-3-em-4-carboxylate (570 mg) was stirred with trifluoroacetic acid (5 ml) and anisole (1.25 ml) for 1 hour. The solution was added dropwise to vigorously stirred water (50 ml). Ether (50 ml) was added and after a few minutes the two phases were separated and the organic phase extracted with water (10 ml). The combined aqueous extracts were washed with ether (2×25 ml), back-washing each time with water (5 ml), concentrated and freeze dried to give the title compound as a foam (255 mg); $\lambda_{max}$ (ethanol) 232.5 ($\epsilon$17700), 313.5 ($\epsilon$21,000); $\nu_{max}$ (Nujol) 3260 (NH), 1770 ($\beta$-lactam); 2500, 1722 (—CO$_2$H), 1668, 1554 (—CONH—), 1668 cm$^{-1}$ (CF$_3$CO$_2$—); $\tau$(DMSO-d6) 0.45 (—COHH), 3.13 (thiazolyl), 3.28 (CH═CH—C≡C—CH$_3$), 4.17 (7H) 4.27 (CH═CH—C≡C—CH$_3$), 4.75 (6H), 5.36 (—OCH$_2$CO$_2$—), 5.74, 6.11 (2-CH$_2$), 7.96 (—C≡C—CH$_3$).

EXAMPLE 2

Diphenylmethyl(6R,7R)-7-[(Z)-2-(t-Butoxycarbonylmethoxyimino)-2-(2-tritylaminothiazol-4-yl)acetamido]-3-[(E)-pent-1-en-3-ynyl]ceph-3-em-4-carboxylate A solution of diphenylmethyl(6R,7R)-7-[(Z)-2-(t-butoxycarbonylmethoxyimino)-2-(2-trityaminothiazol-4-yl)acetamido]-3-[(Z)-pent-1-en-3-ynyl]ceph-3-em-4-carboxylate (90 mg) in toluene (10 ml) was refluxed for 120 hours, under nitrogen. The toluene was evaporated and the residue purified by column chromatography (5 g silica gel). Elution with ethyl acetate:petroleum ether (2:3) gave the title ester as a foam (73 mg), (E:Z, 3:1 by nmr spectroscopic comparison with authentic samples).

EXAMPLE 3

(a)

Diphenylmethyl(6R,7R)-7-[(Z)-2-(Carbamoylmethoxyimino)-2-(2-tritylaminothiazol-4-yl)acetamido]-[(E)-pent-1-en-3-ynyl]ceph-3-em-4-carboxylate A stirred solution of diphenylmethyl(6R,7R)-7-amino-3-[(E)-pent-1-en-3-ynyl]ceph-3-em-4-carboxylate, hydrochloride (432 mg) in tetrahydrofuran (10 ml) was treated with triethylamine (125 $\mu$l). (Z)-2-(Carbamoylmethoxyimino)-2-(2-tritylaminothiazol-4-yl)acetic acid (441 mg), 1-hydroxybenzotriazole hydrate (162 mg) and N,N'-dicyclohexylcarbodiimide (248 mg) were added in that order. After 3 h, the precipitated N,N'-dicyclohexylurea was filtered off, the filtrate evaporated and the residue purified by column chromatography (60 g silica gel). Elution with ethyl acetate:dichloromethane (1:3) gave the title compound as a foam (441 mg); $\nu_{max}$ (CHBr$_3$) 3500, 3398 (NH$_2$+NH), 2215 (C≡C), 1786 ($\beta$-lactam), 1722 (CO$_2$R), 1682, 1528 cm$^{-1}$ (CONH); $\tau$(CDCl$_3$) 4.24 (CH═CH—C≡C), 5.33 (OCH$_2$CONH$_2$), 6.48, 6.60 (2-CH$_2$), 8.02 (C≡CCH$_3$).

(b)

(6R,7R)-7-[(Z)-2-(Carbamoylmethoxyimino)-2-(2-aminothiazol-4-yl)acetamido]-3-[(E)-pent-1-en-3-ynyl]-ceph-3-em-4-carboxylic acid, trifluoroacetate salt Trifluoroacetic acid (4 ml) was added to a stirred solution of the product of stage (a) (375 mg) in anisole (1 ml). After 45 min the reaction mixture was added dropwise to rapidly stirred water (50 ml). After 5 min the aqueous solution was washed with ether (4×50 ml), each time back washing with water (10 ml). The aqueous solution was concentrated to 50 ml and freeze dried to give the title compound as a foam (216 mg); $\lambda_{max}$ (ethanol) 237 nm ($\epsilon$19700) and 319 nm ($\epsilon$28200); $\nu_{max}$ (Nujol) 3300 (NH), 2205 (—C≡C—) and 1772 cm$^{-1}$ ($\beta$-lactam); $\tau$(DMSO-d6) values include 0.14 (—CONH), 2.55, 2.90 (—CONH$_2$), 2.95 (—CH═CH—C≡C), 3.94 (—CH═CH—C≡C) 4.15 (7H), 4.76 (6H), 5.54 (OCH$_2$CONH$_2$), and 7.99 (C≡C—CH$_3$).

EXAMPLE 4

(a)

Diphenylmethyl(6R,7R)-7-[(Z)-2-(t-butoxycarbonylmethoxyimino)-2-(2-tritylaminothiazol-4-yl)acetamido]-3-[(E & Z)-4-phenylbut-1-en-3-ynyl]ceph-3-em-4-carboxylate A mixture of the title compounds (1.37 g) was obtained by the method of Example 1(a) starting from the product of Preparation 1 (2.7 g) and phenylpropynal (1.32 ml) and exhibited $\nu_{max}$ (CHBr$_3$) 3400, 3270 (NH), 2190 (—C≡C—), 1790 ($\beta$-lactam), 1730 (—CO$_2$R), 1682, 1526 cm$^{-1}$ (—CONH—); $\tau$(CDCl$_3$) 3.96 (CH═CH—C≡C—Ph, E isomer), 4.18 (CH═CH—C≡C—Ph, Z isomer), 5.59, 6.04 (2-CH$_2$, Z isomer) and 6.38, 6.50 (2-C$_2$, E isomer).

(b)

Diphenylmethyl(1S,6R,7R)-7-[(Z)-2-(t-butoxycarbonylmethoxyimino)-2-(2-tritylaminothiazol-4-yl)acetamido]-3-[(E)-4-phenylbut-1-en-3-ynyl]ceph-3-em-4-carboxylate, 1-oxide and diphenylmethyl(1S,6R,7R)-7-[(Z)-2-(t-butoxycarbonylmethoxyimino)-2-(2-tritylaminothiazol-4-yl)-acetamido]-3-[(Z)-4-phenylbut-1-en-3-ynyl]ceph-3-em-4-carboxylate, 1-oxide The title compounds were prepared according to the method of Example 1(b) starting with the product of stage (a) (2.15 g). The crude product was purified by chromatography on a column of silica gel (150 g), eluting with a mixture of ethyl acetate and dichloromethane (1:19) to give the second title compound (the Z isomer) as a foam (0.617 g); $\nu_{max}$ (CHBr$_3$) 3390 (NH), 1805 ($\beta$-lactam), 1730 (CO$_2$R), 1680, 1526 (—CONH—), 1066 cm$^{-1}$ (S═O); $\tau$(CDCl$_3$) 2.95 (—CH═CH—C≡C—Ph), 4.18 (—(CH═CHC≡C—Ph), 5.13, 6.46 (2-CH$_2$). Further elution, with the same eluant, gave the first title compound (the E isomer) as a foam (0.417 g); $\nu_{max}$ (CHBr$_3$) 3400 (NH), 2195 (—C≡C—), 1805 ($\beta$-lactam) 1730 (—CO$_2$R), 1680, 1526 (—CONH—), 1066 cm$^{-1}$ (S=O); $\tau$(CDCl$_3$) 4.04 (CH=CH—C≡C—Ph), 6.05, 6.86 (2-CH$_2$).

(c)
Diphenylmethyl(6R,7R)-7-[(Z)-2-(t-butoxycarbonyl-methoxyimino)-2-(2-tritylaminothiazol-4-yl)acetamido]-3-[(E)-4-phenylbut-1-en-3-ynyl]ceph-3-em-4-carboxylate The title compound (310 mg) was prepared as a foam according to the method of Example 1(c) using the second product of stage (b) (the E isomer) (397 mg) and exhibited; $\nu_{max}$ (CHBr$_3$) 3400, 3260 (NH), 2195 (—C≡C—), 1792 ($\beta$-lactam), 1730 (—CO$_2$R), 1682, 1528 cm$^{-1}$ (—CONH—); $\tau$(CDCl$_3$) 3.98 (CH=CH—C≡C—Ph), 6.39, 6.51 (2-CH$_2$).

(d)
Diphenylmethyl(6R,7R)-7-[(Z)-2-(t-butoxycarbonyl-methoxyimino)-2-(2-tritylaminothiazol-4-yl)acetamido]-3-[(Z)-4-phenylbut-1-en-3-ynyl]ceph-3-em-4-carboxylate The title compound (476 mg) was prepared as a foam according to the method of Example 1(c) using the second product of stage (b) the (Z isomer) and exhibited; $\nu_{max}$ (CHBr$_3$) 3400, 3260 (NH), 2185 (—C≡C—), 1790 ($\beta$-lactam) 1730 (—CO$_2$R), 1682, 1528 cm$^{-1}$ (—CONH); $\tau$(CDCl$_3$) 3.08 (CH=CH—C≡C—Ph), 4.20 (CH=CH—C≡C—Ph), 5.60, 6.05 (2-CH$_2$).

(e)
(6R,7R)-7-[(Z)-2-(2-aminothiazol-4-yl-2-(carboxymethoxyimino)-acetamido]-3-[(E)-4-phenylbut-1-en-3-ynyl]ceph-3-em-4-carboxylic acid, trifluoroacetate salt The product of stage (c) (291 mg) was stirred with TFA (4 ml) and anisole (1 ml) for 1 hour. The resulting solution was concentrated (ca 1-2 ml) and added, dropwise to vigorously stirred isopropyl ether (100 ml). The precipitated solid was collected by filtration, washed with ether and dried to give the title compound as a solid (121 mg); $\nu_{max}$(Nujol) 3300 (NH), 2180 (C≡C—), 1720 ($\beta$-lactam), 1720 (—CO$_2$H), 1672 (CF$_3$CO$^-_2$), 1672, 1536 (—CONH), 945 cm$^{-1}$ (—CH=CH—); $\tau$(DMSO-d6) 0.45 (—CONH—), 2.40-2.70 (Ph), 2.76 (CH=CH—C≡C—Ph), 3.16 (thiazolyl), 3.63 (CH=CH—C≡C—Ph), 4.12 (7H), 4.72 (6H), 5.37 (—OCH$_2$CO$_2$H), 6.05, 6.35 (2-CH$_2$).

(f)
(6R,7R)-7-[(Z)-2-(aminothiazol-4-yl)-2-(carboxymethoxyimino)acetamido]-3-[(Z)-4-phenylbut-1-en-3-ynyl]ceph-3-em-4-carboxylic acid, trifluoroacetate salt The title compound (173 mg) was prepared as a solid from the product of stage (d) according to the method of stage (e) and exhibited; $\nu_{max}$ (Nujol) 3300 (NH); 2180 (—C≡C—), 1772 ($\beta$-lactam), 1720 (—CONH—), 1670 (CF$_3$CO$^-_2$), 1670, 1540 cm$^{-1}$ (—CONH—); $\tau$(CDCl$_3$) 0.44 (—CONH—), 2.40-2.60 (Ph), 3.06 (CH=CH—C≡C—Ph) 3.13 (thiazolyl), 3.96 (CH=CH—C≡C—Ph), 4.11 (7H), 4.68 (6H), 5.36 (—OCH$_2$CO$_2$H), 5.64, 5.93 (2-CH$_2$)

EXAMPLE 5

(a)
Diphenylmethyl(6R,7R)-7-[(Z)-2-(t-butoxycarbonyl-methoxyimino)-2-(2-tritylaminothiazol-4-yl)acetamido]-3-[(E & Z)-hex-1-en-3-ynyl]ceph-3-em-4-carboxylate The mixture of title compounds (3.48 g, E:Z, 1:2) were prepared as a foam according to the method of Example 1(a) from the product of Preparation 1 (9.00 g) and 2-pentynal [prepared by Jones oxidation of 2-pentyn-1-ol, according to the general method of S. Galaj and Y-L. Pascal, Bull. Soc. Chim. Fran., 3970 (1972)] (1.18 g). The mixture exhibited $\nu_{max}$(CHBr$_3$) 3400, 3270 (NH), 2270 (C≡C) 1790, ($\beta$-lactam), 1730 (CO$_2$R), 1680, 1526 cm$^{-1}$ (—CONH—); $\tau$(CDCl$_3$) 3.26, 4.42 (CH=CH—C≡C, Z isomer), 4.19 (CH=CH—C≡C, E isomer), 5.71, 6.14 (2-CH$_2$, Z isomer) 6.45, 6.56 (2-CH$_2$, E isomer).

(b)
Diphenylmethyl(1S,6R,7R)-7-[(E)-2-(t-butoxycarbonylmethoxyimino)-2-(2-tritylaminothiazol-4-yl)acetamido]-3-[(Z)-hex-1-en-3-ynyl]ceph-3-em-4-carboxylate, 1-oxide and diphenylmethyl(1S,6R,7R)-7-[(Z)-2-(t-butoxycarbonyl-methoxyimino)-2-(2-tritylaminothiazol-4-yl)acetamido]-3-[(E)-hex-1-en-3-ynyl]ceph-3-em-4-carboxylate, 1-oxide The title compounds were prepared according to the method of Example 1(b) starting with the product of stage (a) (3.42 g). The crude produce was purified on a column of silica gel (500 g) eluting with a mixture of chloroform and ether (9:1) to give the first title compound (the Z isomer) as a foam (1.74 g); $\nu_{max}$ (CHBr$_3$) 3390 (NH), 2200 (—C≡C—), 1804 ($\beta$-lactam), 1730 (—CO$_2$R), 1680, 1526 (—CONH—), 1050 cm$^{-1}$ (S=O); $\tau$(CDCl$_3$) 3.07 (CH=CH—C≡C—), 4.42 (CH=CH—C≡C—), 5.22, 6.54 (2-CH$_2$), 7.65 (CH$_2$CH$_3$) and 8.84 (CH$_2$CH$_3$). Further elution with the same eluant gave the second title compound (the E isomer) as a foam (0.973 g); $\nu_{max}$ (CHBr$_3$) 3400 (NH—), 2210 (—C≡C—), 1804 ($\beta$-lactam), 1680, 1526 (—CONH—), 1062 cm$^{-1}$ (S=O); $\tau$(CDCl$_3$) 4.24 (CH=CH—C≡C—), 6.10, 6.90 (2-CH$_2$), 7.66 (CH$_2$CH$_3$9 and 8.84 (CH$_2$CH$_3$).

(c) Diphenylmethyl (6R,7R)-7-[(Z)-2-(t-butoxycarbonylmethoxyimino)-2-(2-tritylaminothiazol-4-yl)acetamido]-3-[(E)-hex-1-en-3-ynyl]ceph-3-em-4-carboxylate The title compound (0.803 g) was prepared as a foam according to the method of Example 1(c) using the second product of stage (b) (the E isomer) (0.923 g) and exhibited $\nu_{max}$ (CHBr$_3$) 3395, 3260 (NH), 2210 (C≡C), 1790 ($\beta$-lactam), 1730 cm$^{-1}$ (CO$_2$R); $\tau$(CDCl$_3$) 2.74 (—CH=CH—C≡C), 4.19 (—CH=CH—C≡C), 6.46, 6.57 (2-CH$_2$), 7.65 (CH$_2$CH$_3$), 8.83 (CH$_2$CH$_3$).

(d) Diphenylmethyl (6R,7R)-7-[(Z)-2-(t-butoxycarbonylmethoxyimino)-2-(2-tritylaminothiazol-4-yl)acetamido]-3-[(Z)-hex-1-en-3-ynyl]ceph-3-em-4-carboxylate The title compound (1.18 g) was prepared as a foam according to the method of Example 1(c) using the first product of stage (b) (the Z isomer) and exhibited $\nu_{max}$ (CHBr$_3$) 3400, 3270 (NH), 2200 (C≡C), 1790 ($\beta$-lactam), 1730 (CO$_2$R), 1680, 1526 cm$^{-1}$ (—CONH—); $\tau$(CDCl$_3$) 3.25 (CH=CH—C≡C), 4.42 (CH=CH—C≡C), 5.72, 6.15 (2-CH$_2$), 7.64 (CH$_2$CH$_3$), 8.84 (CH$_2$CH$_3$).

(e) (6R,7R)-7-[(Z)-2-(Aminothiazol-4-yl)-2-carboxymethoxyimino)acetamido]-3-[(E)-hex-1-en-3-ynyl]ceph-3-em-4-carboxylic acid, trifluoroacetate salt The title compound (113 mg) was prepared as a foam according to the method of Example 1(e) using the product of stage (c) and exhibited $\nu_{max}$ (Nujol) 1770 ($\beta$-lactam); $\tau$(DMSO-d6) values include 0.46 (—CONH), 2.94 (—CH=CH—C≡C), 3.93 (—CH=CH—C≡C), 4.16 (7H), 4.77 (6H), 5.36 (—OCH$_2$COOH), 7.61 (C≡C—CH$_2$) and 8.87 (C≡C—CH$_2$CH$_3$).

(f) (6R,7R)-7-[(Z)-2-(2-Aminothiazol-4-yl)-2-(carboxymethoxyimino)acetamido]-3-[(Z)-hex-1-en-3-ynyl]ceph-3-em-4-carboxylic acid, trifluoroacetic salt The title compound (284 mg) was prepared as a foam according to the method of Example 1(e) using the product of stage (d) (1.108 g) and exhibited $\nu_{max}$(Nujol) 3280 (NH), 1770 ($\beta$-lactam); $\tau$(DMSO-d6) values include 0.45 (—CONH—), 3.26 (—CH=CH—C≡C), 4.25 (—CH=CH—C≡C—), 4.15 (7H), 4.73 (6H), 5.34 (—OCH$_2$CO$_2$H), 7.58 (C≡C—CH$_2$), and 8.86 (—C≡C—CH$_2$CH$_3$).

(g) (6R,7R)-7-[(Z)-2-(2-Aminothiazol-4-yl)-2-(carboxymethoxyimino)acetamido]-3-[(Z)-hex-1-en-3-ynyl]ceph-3-em-4-carboxylic acid, hydrochloride salt A stirred solution of the product of stage (d) in formic acid (0.8 ml) was treated with 11M hydrochloric acid (56 $\mu$l). After 2.5 h the reaction mixture was filtered and the filtrate was added dropwise to vigorously stirred ether (50 ml). The precipitated solid was collected by filtration, washed with ether and dried in vacuo to give the title compound as a solid (78 mg); $\nu_{max}$ (Nujol) 3280 (—NH), 2200 (C≡C), 1776 ($\beta$-lactam); $\tau$(DMSO-d6) values include 0.27 (NH), 3.24 (—CH=CH—C≡C), 4.24 (—CH=CH—C≡C), 4.17 (7H), 4.72 (6H), 5.28 (OCH$_2$CO$_2$H), 7.68 (C≡C—CH$_2$) and 8.86 (C≡C—CH$_2$CH$_3$).

EXAMPLE 6

(a) Diphenylmethyl (6R,7R)-7-[(Z)-2-(t-butoxycarbonylmethoxyimino)-2-(2-tritylaminothiazol-4-yl)acetamido]-3-[(Z)-4-(trimethylsilyl)but-1-en-3-ynyl]ceph-3-em-4-carboxylate and diphenylmethyl (6R,7R)-7-[(Z)-2-(t-butoxycarbonylmethoxyimino)-2-(2-tritylaminothiazol-4-yl)acetamido]-3-[(E)-4-(trimethylsilyl)but-1-en-3-ynyl]ceph-3-em-4-carboxylate A stirred solution of the product of Preparation 1 (2.70 g) in dichloromethane (30 ml) was treated with saturated sodium bicarbonate solution (5 ml). (Trimethylsilyl)propynal (preparation described in Tett. Lett. 1973 p3963) (0.545 g) was added and the mixture was stirred for 3.5 h. Water (10 ml) and dichloromethane (20 ml) were added and the two phases were separated. The organic phase was washed with 2N hydrochloric acid (50 ml), water (50 ml) and brine (50 ml) and dried (sodium sulphate). The solvent was removed and the residue was subjected to chromatography to give a mixture of the title compounds, as a foam (1.02 g). The isomeric mixture was separated by medium pressure chromatography (150 g silica gel). Elution with ethyl acetate:petrol (1:3→1:2) gave the first title compound as a foam (0.34 g); $\nu_{max}$ (CHBr$_3$) 3400, 3270 (NH), 2135 (C≡C), 1790 cm$^{-1}$ ($\beta$-lactam); $\tau$(CDCl$_3$) values include 1.38 (CONH), 3.23 (CH=CHC≡C), 4.45 (CH=CH—C≡C) 4.13 (7H), 4.92 (6H), 5.21, 5.32 (OCH$_2$CO$_2$—), 9.82 (Si(CH$_3$)$_3$). Further elution gave a mixed fraction (0.09 g). Further elution gave the second title compound as a foam (0.21 g); $\nu_{max}$ (CHBr$_3$) 3400, 3260 (NH), 2150 (C≡C), 1790 cm$^{-1}$ ($\beta$-lactam); $\tau$(CDCl$_3$) values include 1.36 (CONH), 4.19 (—CH=CH—C≡C), 4.12 (7H), 4.93 (6H), 5.21, 5.32 (OCH$_2$CO$_2$), 9.80 (Si(CH$_3$)$_3$).

(b) Diphenylmethyl (6R,7R)-7-[(Z)-2-(t-butoxycarbonylmethoxyimino)-2-(2-tritylaminothiazol-4-yl)acetamido]-3-[(Z)-but-1-en-3-ynyl]ceph-3-em-4-carboxylate A solution of silver nitrate (190 mg) in water (2 ml) was added to a stirred solution of the first product of Stage (a) (378 mg) in ethanol (20 ml), under nitrogen, in the dark, with ice-bath cooling. After 75 mins the pale yellow suspension was dissolved in dichloromethane (50 ml) and the resulting yellow solution was treated, with vigorous stirring, with 5% potassium cyanide solution (8 ml) quickly followed by water (30 ml). After a few minutes the two layers were separated and the aqueous phase was extracted with dichloromethane. The combined organic extracts were washed with water and brine and dried. The solvent was removed and the residue was purified by chromatography to afford the title compound as a foam (241 mg); $\nu_{max}$ (CHBr$_3$) 3400, 3300 (NH), 1790 cm$^{-1}$ ($\beta$-lactam); $\tau$(CDCl$_3$) values include 1.38 (CONH), 3.17 (—CH=CH—C≡C), 4.46 (—CH=CH—C≡C), 5.19, 5.31 (—OCH$_2$CO$_2$), 6.64 (C≡C—H).

(c) Diphenylmethyl (6R,7R)-7-[(Z)-2-(t-butoxycarbonylmethoxyimino)-2-(2-tritylaminothiazol-4-yl)acetamido]-3-[(E)-but-1-en-3-ynyl]ceph-3-em-4-carboxylate The title compound was prepared according to the method of stage (b) starting from the second product of stage (a) (243 mg) and exhibited; $\nu_{max}$ (CHBr$_3$) 3400, 3300 (NH), 1790 cm$^{-1}$ ($\beta$-lactam); $\tau$(CDCl$_3$) values include 1.35 (CONH), 4.25 (CH=CH—C≡C), 4.10 (7H), 4.92 (6H), 5.20, 5.31 (OCH$_2$CO$_2$), 6.51 (C≡C—H).

(d) (6R,7R)-7-[(Z)-2-(2-Aminothiazol-4-yl)-2-(carboxymethoxyimino)acetamido]-3-[(Z)-but-1-en-3-ynyl]ceph-3-em-4-carboxylic acid, trifluoroacetate salt The title compound (432 mg) was prepared from the product of stage (b) (1033 mg) according to the method of Example 1(e) and exhibited; $\nu_{max}$ (Nujol) 3280 (NH), 1772 cm$^{-1}$ ($\beta$-lactam); $\tau$(DMSO-d6) values include 0.42 (CONH), 3.16 (—CH=CH—C≡C—), 4.22 (—CH=CH—C≡C—), 4.15 (7H), 4.72 (6H), 5.35 (OCH$_2$CO$_2$—), 5.48 (C≡C—H).

EXAMPLE 7

(a) Diphenylmethyl (6R,7R)-7-[(Z)-2-methoxycarbonylmethoxyimino-2-(2-tritylaminothiazol-4-yl)acetamido]-3-[(E)-pent-1-en-3-ynyl]ceph-3-em-4-carboxylate A solution of oxalyl chloride (0.14 ml) in dichloromethane (2 ml) was added dropwise over 5 min to a solution of DMF (0.17 ml) in dichloromethane (7 ml) at $-15°$ under nitrogen and with stirring. This solution was stirred at $<-5°$ when a white precipitate formed. This mixture was cooled to $-10°$ and (Z)-2-(Methoxycarbonylmethoxyimino)-2-(2-tritylamino-4-thiazolyl-)acetic acid (0.83 g) was added in one portion. This dissolved to give a clear brown solution which was stirred at $-5°$ for 0.5 h before recooling to $-10°$. Meanwhile N,N-dimethylaniline (0.42 ml) and triethylamine (0.20 ml), were added to a solution of the product of Preparation 7 in dichloromethane (11 ml) at $-25°$ C. The solution of active side chain was added and the mixture allowed to warm 10° over 2.5 h. Water (21 ml) was added and the layers shaken. The organic layer was separated off and washed with 2N hydrochloric acid, water, aq. sodium bicarbonate, and saturated brine respectively. The organic phase was dried (sodium sulphate) and evaporated. The product was purified by chromatography over silica gel eluting with ethyl acetate:petrol to give the title compound as a foam (0.81 g); $\nu_{max}$ (CHBr$_3$) 3393, 3280 (NH), 2215 (C≡C), 1787 cm$^{-1}$ ($\beta$-lactam); $\tau$(CDCl$_3$) values include 1.78 (CONH), 4.10 (7H), 4.20 (—CH=CH—C≡C), 4.92 (6H), 5.12 (—OCH$_2$CO$_2$), 6.25 (—CO$_2$CH$_3$), 8.00 (C≡C—CH$_3$).

(b) (6R,7R)-7-[(Z)-2-methoxycarbonylmethoxyimino-2-(2-aminothiazol-4-yl)acetamido]-3-[(E)-pent-1-en-3-ynyl]-ceph-3-em-4-carboxylic acid Water (6 ml) was added to a solution of the product of Stage (a) in formic acid (15 ml) and the mixture heated to 50° for 15 min. The suspension was allowed to cool to room temperature and then filtered. The solid was washed with 3:1 formic acid:water and the combined washings and filtrate evaporated to give a light brown gum. This gum was triturated with ether and the resultant solid filtered off, washed with ether and dried in vacuo to give the title compound as a white solid (0.33 g); $\nu_{max}$ (Nujol) 3320 (NH), 2220 (C≡C), 1770 cm$^{-1}$ ($\beta$-lactam); $\tau$(DMSO-d6) values include 0.45 (CONH), 2.94 (—CH=CH—C≡C), 3.96 (—CH=CH—C≡C), 4.20 (7H), 4.79 (6H), 5.31 (—OCH$_2$CO$_2$), 6.31 (—CO$_2$CH$_3$), 8.00 (C≡C—CH$_3$)

EXAMPLE 8

(a) Diphenylmethyl (6R,7R)-7-(2-thienyl)acetamido-3-[(E and Z)-4-phenyl-1-buten-3-ynyl]ceph-3-em-4-carboxylate Diphenylmethyl (6R,7R)-7-(2-thienylacetamido)-3-(triphenylphosphoranylidenemethyl)ceph-3-em-4-carboxylate (preparation described in British Patent Specification No. 1342241) (4.69 g) was added portionwise over 4.5 h to a stirred solution of phenylpropynal (3.75 ml) in dichloromethane (50 ml). After stirring for a further 21 h the mixture was diluted with dichloromethane (100 ml) and washed with 10% aqueous sodium metabisulphite solution (2×150 ml), and brine (150 ml). After drying (sodium sulphate) the solvent was removed and the residue was purified by chromatography (200 g silica gel). Elution with ethyl acetate:dichloromethane mixtures gave the title compounds (3:2) as an orange solid (2.12 g); $\nu_{max}$ (Nujol) 3280 (NH), 2180 (C≡C), 1777 cm$^{-1}$ ($\beta$-lactam); $\tau$(CDCl$_3$) values include 3.49, 3.58 (CONH), 3.15 ((Z)—CH=CH—C≡C), 4.00 ((E)—CH=CH—C≡C), 4.22 (Z)—CH=CH—C≡C).

(b) Diphenylmethyl (1S,6R,7R)-7-(2-thienyl)acetamido-3-[(Z)-4-phenyl-1-buten-3-ynyl]ceph-3-em-4-carboxylate, 1-oxide and diphenylmethyl(1S,6R,7R)-7-(2-thienyl)acetamido-3-[(E)-4-phenyl-1-buten-3-ynyl]ceph-3-em-4-carboxylate, 1-oxide The title compounds were prepared from the product of stage (a) (365 mg) according to the method of Example 1(b). The crude product was purified by chromatography (20 g silica gel), eluting with ethyl acetate:dichloromethane (1:19). Eluting the column gave firstly the first title compound (the Z isomer) as a solid (175 mg); $\nu_{max}$ (Nujol) 3280 (NH), 2180 (C≡C), 1778 cm$^{-1}$ ($\beta$-lactam); $\tau$(DMSO-d6) values include 1.54 (CONH), 3.11 (—CH=CH—C≡C), 4.02 (7H and —CH=CH—C≡C), 4.91 (6H). Further elution gave the second title compound (the E isomer) as a solid (93 mg); $\nu_{max}$ (Nujol) 3300 (NH), 2185 (C≡C), 1796 cm$^{-1}$ ($\beta$-lactam); $\tau$(DMSO-d6) values include 1.46 (CONH), 3.60 (—CH=CH—C≡C), 4.00 (7H), 4.93 (6H).

(c) Diphenylmethyl (6R,7R)-7-(2-thienyl)acetamido-3-[(Z)-4-phenyl-1-buten-3-ynyl]ceph-3-em-4-carboxylate A solution of phosphorus tribromide (0.12 ml) in dichloromethane (5 ml) was added dropwise to a stirred solution of the first product of stage (b) (the Z isomer) (719 mg) in dichloromethane (60 ml) at $-40°$, under nitrogen. After 15 mins the reaction mixture was allowed to warm to 0° over 60 mins and then maintained at between 0° and 5° for 60 mins before being poured into ice-cold saturated sodium bicarbonate solution (100 ml). Dichloromethane (125 ml) was added and the two layers were separated. The organic phase was washed with 2N hydrochloric acid (150 ml) and brine (150 ml) and dried (sodium sulphate). The solvent was removed and the residue was purified by chromatography (40 g silica gel). Elution with ethyl acetate:dichloromethane (1.19) gave the title compound as a solid (447 mg); $\nu_{max}$ (CHBr$_3$) 3400 (NH), 2185 (C≡C), 1788 cm$^{-1}$ ($\beta$-lactam); $\tau$(CDCl$_3$) values include 3.14 (—CH=CH—C≡C), 3.56 (NH), 4.18 (7H), 4.22 (—CH=CH—C≡C), 5.00 (6H).

(d) Diphenylmethyl (6R,7R)-7-(2-thienyl)acetamido-3-[(E)-4-phenyl-1-buten-3-ynyl]ceph-3-em-4-carboxylate The title compound (206 mg) was prepared as a foam from the second product of stage (b) (the E isomer) according to the method of stage (c) and exhibited; $\nu_{max}$ (CHBr$_3$) 3400 (NH), 2195 (C≡C), 1786 cm$^{-1}$ ($\beta$-lactam); $\tau$(CDCl$_3$) values include 3.62 (CONH), 3.98 (—CH=CH—C≡C), 4.16 (7H), 5.01 (6H), 6.17 (—CH$_2$CO).

(e)
(6R,7R)-7-(2-thienyl)acetamido-3-[(Z)-4-phenyl-1-buten-3-ynyl]ceph-3-em-4-carboxylic acid A stirred solution of the product of Stage (c) in anisole (0.5 ml) was treated with TFA (2.0 ml). After 15 mins the solution was evaporated and the residue was dissolved in ethyl acetate (10 ml). The solution was washed with dilute sodium bicarbonate solution (2×20 ml). The combined aqueous extracts were washed with ethyl acetate (10 ml) and then acidified to pH2, by the addition of 2N hydrochloric acid, in the presence of ethyl acetate (25 ml). The two layers were separated and the aqueous phase was extracted with ethyl acetate (25 ml). The combined organic extracts were dried (sodium sulphate) and evaporated to give the title compound as a solid (122 mg); $\nu_{max}$ (Nujol) 3280 (NH), 2180 (C≡C), 1776 cm$^{-1}$ ($\beta$-lactam; $\tau$(DMSO-d6) includes 0.84 (NH), 3.08 (—CH=CH—C≡C), 3.97 (—CH=CH—C≡C), 4.24 (7H), 4.74 (6H).

EXAMPLE 9

(a)
Diphenylmethyl-(6R,7R)-7-(2-thienyl)acetamido-3-[(E and Z)-pent-1-en-3-ynyl]ceph-3-em-4-carboxylate Diphenylmethyl (6R,7R)-7-(2-thienylacetamido)-3-(triphenylphosphoranylidenemethyl)ceph-3-em-4-carboxylate (1.00 g) was added portionwise over 1.5 h to a stirred solution of 2-butynal (0.48 ml) in dichloromethane (10 ml), under nitrogen. After stirring for a further 21 h the solvent and excess aldehyde were removed and the residue was purified by chromatography (40 g silica gel). Elution with ethyl acetate:dichloromethane (1:19) gave the title compounds (3:2) as a solid (0.20 g) which were characterised as their sulphoxides in the following experiment.

(b) Diphenylmethyl
(1S,6R,7R)-7-(2-thienyl)acetamido-3-[(Z)-pent-1-en-3-ynyl]ceph-3-em-4-carboxylate, 1-oxide and diphenylmethyl
(1S,6R,7R)-7-(2-thienyl)acetamido-3-[(E)-pent-1-en-3-ynyl]ceph-3-em-4-carboxylate, 1-oxide The title compounds were prepared from the product of stage (a) (185 mg) according to the method of Example 1(b). The crude product was purified by chromatography (20 g silica gel). Elution with ethyl acetate:dichloromethane (1:7) gave the first title compound (the Z isomer) as a solid (84 mg); $\nu_{max}$ (Nujol) 3290 (NH), 1782 cm$^{-1}$ ($\beta$-lactam); $\tau$(DMSO-d6) values include 1.50 (NH), 2.32 (—CH=CH—C≡C), 4.04 (7H), 4.32 (—CH=CH—C≡C), 4.97 (6H), 7.99 (C≡C—CH$_3$). Further elution gave the second title compound (the E isomer) as a solid (37 mg); $\tau$(DMSO-d6) values include 1.51 (NH), 2.94 (—CH=CH—C≡C), 3.92 (—CH=CH—C≡C), 4.06 (7H), 4.99 (6H), 7.99 (C≡C—CH$_3$).

EXAMPLE 10

(a) Diphenylmethyl
(6R,7R)-7-(2-thienyl)acetamido-3-[(E and Z)-4-trimethylsilyl)but-1-en-3-ynyl]ceph-3-em-4-carboxylate Diphenylmethyl (6R,7R)-7-(2-thienylacetamido)-3-(triphenylphosphoranylidenemethyl)ceph-3-em-4-carboxylate (1.00 g) was added portionwise over 1 h to a stirred solution of (trimethylsilyl)propynal (0.33 g) in dichloromethane (10 ml). After stirring for a further 22 h the mixture was evaporated and the residue was purified by chromatography (40 g silica gel). Elution with ethyl acetate:dichloromethane (1:49) gave the title compounds (2:1) as a foam (0.13 g); $\nu_{max}$ (CHBr$_3$) 3400 (NH), 1790 cm$^{-1}$ ($\beta$-lactam); $\tau$(CDCl$_3$) values include 3.21 (—CH=CH—C≡C—), 3.69 (NH), 4.19 (7H), 4.42 (—CH=CH—C≡C), 4.99 (6H).

EXAMPLE 11

(a) Diphenylmethyl
(6R,7R)-7-[(Z)-2-(diphenylmethoxycarbonylmethoxyimino)-2-(2-tritylaminothiazol-4-yl)acetamido]-3-[(Z)-4-(trimethylsilyl)but-1-en-3-ynyl]-ceph-3-em-4-carboxylate and diphenylmethyl
(6R,7R)-7-[(Z)-(diphenylmethoxycarbonylmethoxyimino)-2-(2-tritylaminothiazol-4-yl-)acetamido]-3-[(E)-4-(trimethylsilyl)but-1-en-3-ynyl]ceph-3-em-4-carboxylate The title compounds were prepared according to the method of Example 6(a) from the product of Preparation 4 (15.00 g) and (trimethylsilyl)propynal (2.79 g).

The mixture of the title compounds obtained from the first chromatographic purification step was separated by medium pressure chromatography (1000 g silica gel). Elution with ethyl acetate:petrol (1:3→2:5) gave the first title compound (the Z isomer) as a foam (3.11 g); $\nu_{max}$ (CHBr$_3$) 3390, 3290 (NH), 2140 (C≡C), 1790 cm$^{-1}$ ($\beta$-lactam); $\tau$(CDCl$_3$) values include 1.90 (CONH), 3.16 (—CH=CH—C≡C), 4.10 (7H), 4.37 (—CH=CH—C≡C), 4.98 (6H), 4.95, 5.10 (—OCH$_2$CO$_2$—), 9.81 (Si(CH$_3$)$_3$). Further elution gave a mixed fraction as a foam (1.22 g). Further elution gave the second title compound (the E isomer) as a foam (1.49 g); $\nu_{max}$ (CHBr$_3$) 3390, 3280 (NH), 2130 (C≡C), 1788 cm$^{-1}$ ($\beta$-lactam); $\tau$(CDCl$_3$) values include 1.96 (CONH), 4.09 (7H), 4.26 (—CH=CH—C≡C), 4.95, 5.12 (OCH$_2$CO$_2$—), 5.01 (6H), 9.78 (Si(CH$_3$)$_3$).

(b) Diphenylmethyl
(6R,7R)-7-[(Z)-2-(diphenylmethoxycarbonylmethoxyimino)-2-(2-tritylaminothiazol-4-yl)acetamido]-3-[(E)-but-1-en-3-ynyl]ceph-3-em-4-carboxylate The title compound (1.01 g) was prepared as a foam from the second product of stage (a) (the E isomer) (1.795 g) according to the method of Example 6(b) and exhibited; $\nu_{max}$ (CHBr$_3$) 3400 (NH), 3305 (C≡C—H), 1790 cm$^{-1}$ ($\beta$-lactam); $\tau$(CDCl$_3$) values include 1.93 (CONH), 4.06 (7H), 4.33 (—CH=CH—C≡C), 4.94, 5.14 (—OCH$_2$CO$_2$—), 5.00 (6H), 6.85 (C≡C—H).

(c)
(6R,7R)-7-[(Z)-2-(2-Aminothiazol-4-yl)-2-carboxymethoxyimino)acetamido]-3-[(E)-but-1-en-3-ynyl]-ceph-3-em-4-carboxylic acid Water (8 ml) was added dropwise to a stirred solution of the product of Stage (b) (687 mg) in formic acid (20 ml) and the mixture was heated for 50° for 1 h. On cooling, the mixture was filtered. The filtrate was concentrated and added dropwise to vigorously stirred ether (300 ml). The mother liquors were decanted and the solid was washed with more ether (300 ml). The solid was collected by filtration, washed thoroughly with ether and dried in vacuo to give the title compound as a solid (167 mg); $\lambda_{max}$ (EtOH) 229 nm ($\epsilon$18,100) and 312.5 nm ($\epsilon$19,500); $\tau$(acetone-d6) values include 1.40 (CONH), 2.57 (—CH=CH—C≡C), 3.94

(—CH=CH—C≡C—), 4.00 (7H), 4.70 (6H), 5.22 (—OCH₂CO₂—), 6.36 (—C≡C—H).

EXAMPLE 12

(a) Diphenylmethyl (6R,7R)-7-[(Z)-2-(diphenylmethoxycarbonylmethoxyimino)-2-(2-tritylaminothiazol-4-yl)acetamido]-3-[(E and Z)-hex-1-en-3-ynyl]ceph-3-em-4-carboxylate The mixture of title compounds (2:1, 0.81 g) was prepared from the product of Preparation 4 (1.91 g) and 2-pentynal (0.23 g) according to the method of Example 1(a) and exhibited; $\nu_{max}$ (CHBr₃) 3400, 3280 (NH), 1780 cm⁻¹ (β-lactam); τ(CDCl₃) values include 1.98 (CONH), 3.16 (—CH=CH—C≡C), 4.12 (7H), 4.36 (—CH=CH—C≡C), 4.99 (6H), 4.98, 5.10 (—OCH₂CO₂—), 7.66 (C≡C—CH₂—), 8.86 (C≡C—CH₂CH₃).

(b) Diphenylmethyl (1S,6R,7R)-7-[(Z)-2-(diphenylmethoxycarbonylmethoxyimino)-2-(2-tritylaminothiazol-4-yl)acetamido]-3-[(Z)-hex-1-en-3-ynyl]ceph-3-em-4-carboxylate, 1-oxide and diphenylmethyl (1S,6R,7R)-7-[(Z)-2-(diphenylmethoxycarbonylmethoxyimino)-2-(2-tritylaminothiazol-4-yl)acetamido]-3-[(E)-hex-1-en-3-ynyl]ceph-3-em-4-carboxylate, 1-oxide The title compounds were prepared from the product of stage (a) according to the method of Example 1(b). Chromatography gave first the first title compound (the Z isomer) as a foam (2.76 g); $\nu_{max}$ (CHBr₃) 3390 (NH), 2205 (C≡C), 1802 cm⁻¹ (β-lactam); τ(CDCl₃) values include 2.12 (—CONH), 3.04 (—CH=CH—C≡C), 3.93 (7H), 4.38 (—CH=CH—C≡C), 5.05 (—OCH₂CO₂—), 5.51 (6H), 7.65 (C≡C—CH₂—), 8.86 (C≡C—CH₂CH₃). Further elution gave a mixed fraction as a yellow foam (0.40 g). Further elution gave the second title compound (the E isomer) as a foam (1.15 g); $\nu_{max}$ (CHBr₃) 3390 (NH), 2210 (C≡C), 1802 cm⁻¹ (β-lactam); τ(CDCl₃) values include 2.18 (—CONH), 3.94 (7H), 4.26 (—CH=CH—C≡C), 5.07 (—OCH₂CO₂—), 5.54 (6H), 7.66 (—C≡C—CH₂), 8.83 (C≡C—CH₂—CH₃).

(c) Diphenylmethyl (6R,7R)-7-[(Z)-2-(diphenylmethoxycarbonylmethoxyimino)-2-(2-tritylaminothiazol-4-yl)acetamido]-3-[(E)-hex-1-en-3-ynyl]ceph-3-em-4-carboxylate The title compound (0.89 g) was prepared as a foam from the second product of stage (b) (the E isomer) (1.08 g) according to the method of Example 1(c) and exhibited; $\nu_{max}$ (CHBr₃) 3400 (NH), 1790 cm⁻¹ (β-lactam); τ(CDCl₃) values include 1.95 (—CONH), 4.10 (7H), 4.27 (—CH=CH—C≡C), 5.00 (6H), 4.95, 5.13 (—OCH₂CO₂—), 7.61 (C≡C—CH₂), 8.81 (C≡C—CH₂CH₃).

(d) (6R,7R)-7-[(Z)-2-(2-Aminothiazol-4-yl)-2-carboxymethoxyimino)acetamido]-3-[(E)-hex-1-en-3-ynyl]ceph-3-em-4-carboxylic acid The title compound (361 mg) was prepared as a solid from the product of stage (c) (828 mg) according to the method of Example 11(c) and exhibited; $\nu_{max}$ (Nujol) 3300 (NH), 2200 (C≡C), 1770 cm⁻¹ (β-lactam); τ(DMSO-d6) values include 0.48 (CONH), 2.94 (—CH=CH—C≡C), 3.92 (—CH=CH—C≡C), 4.17 (7H), 4.77 (6H), 7.60 (C≡C—CH₂—), 8.87 (C≡C—CH₂CH₃).

EXAMPLE 13

(a) Diphenylmethyl(6R,7R)-7-[(Z)-2-(t-butoxycarbonylmethoxyimino)-2-(2-tritylaminothiazol-4-yl)acetamido]-3-[(Z)-5-ethoxy-5-oxo-pent-1-en-3-ynyl]-ceph-3-em-4-carboxylate and diphenylmethyl(6R,7R)-7-[(Z)-2-(t-butoxycarbonylmethoxyimino)-2-(2-tritylaminothiazol-4-yl)acetamido]-3-[(E)-5-ethoxy-5-oxo-pent-1-en-3-ynyl]-ceph-3-em-carboxylate To a solution of (6R,7R)-[7-((Z)-2-(t-butoxycarbonylmethoxy)imino-2-(2-tritylamino-4-thiazolyl)acetamido)-4-diphenylmethoxycarbonylceph-3-em-3-ylmethyl]triphenylphosphonium iodide (3.30 g) (prepared according to the method of Preparation 1 from the 3-iodomethyl analogue) in methylene chloride (30 ml) was added to a solution of the product of Preparation 16 (3.30 g, containing 40% of the product of Preparation 15) in methylene chloride (16 ml). Saturated aqueous sodium bicarbonate (16 ml) was added and the mixture stirred for 18 h. The organic phase was separated off and washed successively with 2N-hydrochloric acid (25 ml), water (40 ml) and brine (40 ml). The organic solution was dried and evaporated to a foam (4.72 g), which was purified by chromatography on silica gel (100 g) eluting with chloroform containing 0.02% ethyl acetate to give a foam (1.48 g). The foam was combined with more material (0.90 g) obtained from a similar experiment and subjected to medium pressure chromatography on silica gel (150 g). Elution with ethyl acetate:petrol (2:1) gave the first title compound (the Z isomer) as a foam (0.87 g); $\nu_{max}$ (CHBr₃) 3395, 3262 (NH), 2203 (C≡C), 1794 cm⁻¹ (β-lactam); τ(CDCl₃) values include 1.30 (CONH), 3.05 (CH=CH—C≡C), 4.06 (7H), 4.43 (—CH=CH—C≡C), 4.89 (6H), 5.24 (—OCH₂CO₂—).

Further elution gave the second title compound (the E isomer) as a foam (0.73 g); $\nu_{max}$ (CHBr₃) 3395, 3262 (NH), 2203 (C≡C), 1795 cm⁻¹ (β-lactam). τ(CDCl₃) values include 1.29 (CONH), 4.06 (7H), 4.21 (—CH=CH—C≡C), 4.90 (6H) 5.20, 5.30 (—OCH₂CO₂—).

(b) (6R,7R)-7-[(Z)-2-Carboxymethoxyimino-2-(2-aminothiazol-4-yl)acetamido]-3-[(Z)-5-ethoxy-5-oxo-pent-1-en-3-ynyl]ceph-3-em-4-carboxylic acid The title compound (0.33 g) was prepared as a solid from the first product of stage (a) (the Z isomer) according to the method of Example 1(e) and exhibited; $\nu_{max}$ (Nujol) 3300 (NH), 2190 (C≡C), 1776 (β-lactam), 1720 cm⁻¹ (CO₂Et); τ(DMSO-d6) values include 0.42 (—CONH), 2.92 (—CH=CH—C≡C), 4.05 (—CH=CH—C≡C), 4.11 (7H), 4.69 (6H), 5.37, (—OCH₂CO₂—), 5.79 (C≡CCO₂CH₂—).

(c) (6R,7R)-7-[(Z)-2-Carboxymethoxyimino-2-(2-aminothiazol-4-yl)acetamido]-3-[(E)-5-ethoxy-5-oxo-pent-1-en-3-ynyl]ceph-3-em-4-carboxylic acid The title compound (0.18 g) was prepared as a foam from the second product of stage (a) (the E isomer) according to the method of Example 1(e) and exhibited; $\nu_{max}$ (Nujol) 3280 (NH), 2190 (C≡C), 1772 cm⁻¹ (β-lactam); τ(DMSO-d6) values include 0.41 (—CONH—), 3.10 (—CH=CH—C≡C), 3.73 (—CH=

CH—C≡C), 4.08 (7H), 4.71 (6H), 5.36 (—OCH$_2$CO$_2$—), 5.78 (C≡C—CO$_2$CH$_2$—).

EXAMPLE 14

(a)

Diphenylmethyl(6R,7R)-7-[(Z)-2-(t-butoxycarbonyl-methoxyimino)-2-(2-tritylaminothiazol-4-yl)acetamido]-3-[(E and Z)-5-diphenylmethoxy,5-oxo-pent-1-en-3-ynyl]ceph-3-em-4-carboxylate The mixture of title compounds (E:Z, 1:1) (0.24 g) was prepared according to the method of Example 13(a) using the product of Preparation 14 (0.24 g) in place of the product of Preparation 16 and exhibited; $\nu_{max}$ (CHBr$_3$) 3395, 3265 (NH), 2205 (C≡C), 1795 cm$^{-1}$ ($\beta$-lactam); $\tau$(CDCl$_3$) values include 1.26, 1.28 (—CONH), 4.06 (7H), 4.22 (—CH=CH—C≡C), (E)), 4.43 (—CH=CH—C≡C—, (Z)), 4.91 (6H) 5.26 (—OCH$_2$CO$_2$—).

(b)

(6R,7R)-7-[(Z)-2-Carboxymethoxyimino-2-(2-aminothiazol-4-yl)acetamido]-3-[(E) and Z)-4-carboxy-but-1-en-3-ynyl]ceph-3-em-4-carboxylic acid The product of Stage (a) (0.50 g) in anisole (1 ml) was treated with trifluoroacetic acid (4.33 ml) at 5° with stirring. After 0.5 h the mixture was added dropwise onto rapidly stirred water (300 ml). The resultant suspension was filtered, partially evaporated and finally freeze dried to give the title compounds as a foam (70 mg) (E:Z, 1:1); $\nu_{max}$ (Nujol) 3300 (NH), 2200 (C≡C), 1776 cm$^{-1}$ ($\beta$-lactam); $\tau$(DMSO-d6) values include 0.43 (—CONH), 2.66 (—CH=CH—C≡C, (E)) 2.96 (—CH=CHC≡C (Z)), 3.76 (—CH=CH—C≡C, (E)), 4.08 (—CH=CH—C≡C, (Z)), 4.12 (7H), 4.69 (6H), 5.38 (—OCH$_2$—CO$_2$—).

EXAMPLE 15

(a)

Diphenylmethyl(6R,7R)-7-formamido-3-[(Z)-hex-1-en-3-ynyl]ceph-3-em-4-carboxylate A stirred solution of (6R,7R)-[4-diphenylmethoxycarbonyl-7-formamidoceph-3-em-ylmethyl]triphenylphosphonium bromide (15.00 g) (preparation described in British Patent Specification No. 1342241) in dichloromethane (250 ml) was treated with saturated sodium bicarbonate solution (75 ml). After a few minutes, 2-pentynal (3.28 g) was added, in one portion, and the mixture was stirred for ca 19 h. The two layers were separated and the organic phase was washed with 2N hydrochloric acid (250 ml), water (250 ml) and brine (250 ml) and dried (sodium sulphate). The solvent was removed and the residue was purified by chromatography (750 g silica gel). Elution with ethyl acetate:dichloromethane (1:19→1:14) gave the title compound as a solid (1.72 g); $\nu_{max}$ (CHBr$_3$) 3410 (NH), 2200 (C≡C), 1783 cm$^{-1}$ ($\beta$-lactam); $\tau$(CDCl$_3$) values include 1.76 (H-CO), 3.26 (—CH=CH—C≡C), 3.54 (NH), 4.14 (7H), 4.42 (—CH=CH—C≡C), 4.98 (6H), 7.66 (C≡C—CH$_2$13 ).

(b)

Diphenylmethyl(6R,7R)-7-formamido-3-[(E)-hex-1-en-3-ynyl]ceph-3-em-4-carboxylate A solution of the product of Stage (a) (1.19 g) and a crystal of iodine in toluene (100 ml) was heated under reflux for 5.75 h (fresh crystals of iodine were added after 2 h and 4 h). The solvent was removed and the residue was purified by chromatography (50 g silica gel). Elution with ethyl acetate:dichloromethane (1:9) gave a mixture (0.24 g). Further elution gave the title compound as a solid (0.66 g); $\nu_{max}$ (CHBr$_3$) 3410 (NH), 2205 (C≡C), 1784 cm$^{-1}$ ($\beta$-lactam) $\tau$(CDCl$_3$) values include 1.82 (HCO), 3.44 (NH), 4.13 (7H), 4.20 (CH=CH—C≡C), 5.04 (6H), 7.67 (C≡C—CH$_2$).

(c)

Diphenylmethyl(6R,7R)-7-Amino-3-[(E)-hex-1-en-3-ynyl]ceph-3-em-4-carboxylate, hydrochloride A stirred suspension of the product of Stage (b) (633 mg) in methanol (5 ml) and ether (5 ml) was treated dropwise with phosphorous oxychloride (250 $\mu$l) with ice-bath cooling. After 90 mins the ice-bath was removed and stirring continued for 40 mins at room temperature. The solution was concentrated and added to vigorously stirred ether (75 ml). The precipitated solid was collected by filtration, washed thoroughly with ether and dried in vacuo to give the title compound as a solid (442 mg); $\nu_{max}$ (Nujol) 2600 (NH$_3^+$), 2200 (C≡C), 1783 cm$^{-1}$ ($\beta$-lactam); $\tau$(DMSO-d6) values include 2.93 (CH=CH—C≡C), 3.74 (—CH=CH—C≡C), 4.66, 4.78 (6H,7H), 7.60 (—C≡C—CH$_2$—).

(d)

Diphenylmethyl(6R,7R)-7-[(Z)-2-diphenylmethoxycarbonylmethoxyimino)-2-(2-tritylaminothiazol-4-yl)acetamido]-3-[(E)-hex-1-en-3-ynyl]-ceph-3-em-4-carboxylate The title compound (224 mg) was prepared as a foam from the product of stage (c) (423 mg) according to the method of Example 3(a) and exhibited; $\nu_{max}$ (CHBr$_3$) 3400 (NH), 1790 cm$^{-1}$ ($\beta$-lactam); $\tau$(CDCl$_3$) values include 1.95 (—CONH), 4.10 (7H), 4.27 (—CH=CH—C≡C), 5.00 (6H), 4.95, 5.13 (—OCH$_2$CO$_2$—), 7.61 (C≡C—CH$_2$—).

EXAMPLE 16

(a)

Diphenylmethyl(6R,7R)-7-[(Z)-2-(trityloxyimino)-2-(2-tritylaminothiazol-4-yl)acetamido]-3-[(E)-pent-1-en-3-ynyl]ceph-3-em-4-carboxylate A solution of oxalyl chloride (0.14 ml) in dichloromethane (2 ml) was added dropwise over 10 min to a stirred solution of DMF (0.3 ml) in dichloromethane (3 ml) at −15°, under nitrogen. After 30 min at <−5° the white suspension was cooled to −10° and (Z)-2-(trityloxyimino)-2-(2-tritylamino-4-thiazolyl)acetic acid (1.126 g) was added in one portion. The resulting clear yellow solution was maintained at −5° to 0° for 30 min before recooling to −10°. This solution was added over 1 min to a stirred solution of the product of Preparation 7 and N,N-dimethylaniline (0.64 ml) in dichloromethane (5 ml) at −25°. The reaction mixture was allowed to warm to 5° during 1.5 h and partitioned between dichloromethane (100 ml) and 2M hydrochloric acid (100 ml). The organic phase was separated, washed with 2M hydrochloric acid, water, sodium bicarbonate solution, water and brine (100 ml of each) and dried (sodium sulphate). The solvent was evaporated and the residue purified by chromatography (60 g silica gel). Elution with ethyl acetate:dichloromethane (1:50) afforded the title compound as a foam (1.25 g); $\lambda_{max}$ (EtOH) 321.5 nm (ε26,300); $\nu_{max}$ (CHBr$_3$) 3400 (NH), 2220 (C≡C), 1790 cm$^{-1}$ (β-lactam); τ(CDCl$_3$) values include 3.97 (7H), 4.28 (—CH=CH—C≡C), 4.92 (6H), 8.02 (C≡C.CH$_3$).

(b) (6R,7R)-7-[(Z)-2-(Hydroxyimino)-2-(2-aminothiazol-4-yl)acetamido]-3-[(E)-pent-1-en-3-ynyl]ceph-3-em-4-carboxylic acid, trifluoroacetate salt TFA (8 ml) was added to a stirred solution of the product of stage (a) (1.16 g) in anisole (2 ml). After 45 min the reaction mixture was added dropwise to rapidly stirred water (100 ml). After 5 min the aqueous solution was washed with ether (4×100 ml), each time back washing with water (10 ml). The aqueous solution was concentrated to 100 ml and freeze dried to give the title compound as a foam (143 mg). The ether extracts were evaporated and the residue treated with TFA (4 ml) and anisole (1 ml) as above to afford more of the title compound as a foam (181 mg); $\nu_{max}$ (Nujol) 3280 (NH), 2210 (C≡C), 1770 cm$^{-1}$ (β-lactam); τ(DMSO-d6) values include 0.46 (CONH), 2.93 (—CH=CH—C≡C), 3.91 (—CH=CH—C≡C), 4.19 (7H), 4.79 (6H), 7.98 (C≡C—CH$_3$).

EXAMPLE 17

(a) Diphenylmethyl (6R,7R)-7-[(Z)-2-(ethoxyimino)-2-(2-tritylaminothiazol-4-yl)acetamido]-3-[(E)-pent-1-en-3-ynyl]ceph-3-em-4-carboxylate The title compound (582 mg) was prepared as a foam starting from (Z)-2-(ethoxyimino)-2-(2-tritylaminothiazol-4-yl)acetic acid (755 mg) and the product of Preparation 7 (700 mg) according to the method of example 16(a) and exhibited; $\nu_{max}$ (CHBr$_3$) 3400 (NH), 2216 (C≡C), 1790 cm$^{-1}$ (β-lactam); τ(CDCl$_3$) values include 3.15 (CONH), 4.06 (7H), 4.23 (—CH=CH—C≡C), 4.93 (6H), 5.66 (—OCH$_2$—), 8.02 (C≡C—CH$_3$), 8.66 (O—CH$_2$CH$_3$).

(b) (6R,7R)-7-[(Z)-2-(ethoxyimino)-2-(2-aminothiazol-4-yl)acetamido]-3-[(E)-pent-1-en-3-ynyl]ceph-3-em-4-carboxylic acid The title compound (288 mg) was prepared as a solid from the product of stage (a) according to the method of Example 7(b) and exhibited; $\nu_{max}$ (Nujol) 3300 (NH), 2210 (C≡C), 1770 cm$^{-1}$ (β-lactam); τ(DMSO-d6) values 0.44 (CONH), 2.94 (—CH=CH—C≡C), 3.93 (—CH=CH—C≡C), 4.19 (7H), 4.78 (6H), 5.87 (—OCH$_2$—), 7.98 (C≡C—CH$_3$), 8.73 (—OCH$_2$CH$_3$).

EXAMPLE 18

(a) Diphenylmethyl (6R,7R)-7-[(Z)-2-(t-butoxycarbonylmethoxyimino)-2-(2-furyl)acetamido]-3-[(E)-pent-1-en-3-ynyl]ceph-3-em-4-carboxylate (Z)-2-(t-Butoxycarbonylmethoxyimino)-2-(2-furyl)acetic acid (582 mg), 1-hydroxybenzotriazole hydrate (338 mg) and N,N'-dicyclohexylcarbodiimide (516 mg) were added in that order to a stirred solution of the product of Preparation 8 in THF (15 ml). After 2 h the reaction mixture was filtered, the filtrate evaporated and the residue dissolved in ethyl acetate and refiltered. The ethyl acetate was evaporated and the residue purified by chromatography (60 g silica gel). Elution with ethyl acetate:benzene (1:10) gave the title compound as a foam (1.062 g); $\lambda_{max}$ (EtOH), 288.5 nm (ε19,600) and 326.nm (ε20,500); $\nu_{max}$ (CHBr$_3$) 3380, 3260 (NH), 2220 (C≡C), 1790 cm$^{-1}$ (β-lactam); τ(CDCl$_3$) values include 1.32 (CONH), 4.08 (7H), 4.21 (—CH=CH—C≡C); 4.89 (6H), 5.28 (—OCH$_2$CO$_2$—), 8.02 (C≡C—CH$_3$).

(b) (6R,7R)-7-[(Z)-2-(carboxymethoxyimino)-2-(2-furyl)acetamido]-3-[(E)-pent-1-en-3-ynyl]ceph-3-em-4-carboxylic acid TFA (8 ml) was added to a stirred solution of the product of stage (a) (992 mg) in anisole (2 ml). After 45 min the solution was evaporated, the residue azeotroped with toluene (20 ml) and dissolved in ethyl acetate. The organic solution was extracted with sodium bicarbonate solution (3×50 ml). The combined aqueous extracts were washed with ethyl acetate (100 ml) and acidified to pH1.5 with 2M hydrochloric acid under ethyl acetate (100 ml). The layers were separated and the aqueous phase extracted with ethyl acetate (2×75 ml). The combined organic extracts were washed with water (2×200 ml), dried (sodium sulphate) and evaporated to give the title compound as a foam (669 mg); $\nu_{max}$ (Nujol) 3250 (NH), 2205 (C≡C), 1770 cm$^{-1}$ (β-lactam); τ(DMSO-d6) values include 0.24 (NH), 2.90 (—CH=CH—C≡C), 3.91 (—CH=CH—C≡C), 4.14 (7H), 4.72 (6H), 5.30 (—OCH$_2$CO$_2$—), 7.96 (C≡C—CH$_3$).

EXAMPLE 19

(a) Diphenylmethyl(6R,7R)-7-[(Z)-2-(methoxyimino)-2-(2-furyl)acetamido]-3-[(E)-pent-1-en-3-ynyl]ceph-3-em-4-carboxylate The title compound (555 mg) was prepared as a solid from (Z)-2-(2-furyl)-2-(methoxyimino)acetic acid (355 mg) and the product of Preparation 8 (886 mg) according to the method of Example 3(a) and exhibited; $\nu_{max}$ (CHBr$_3$) 3400 (NH), 2220 (C≡C), 1788 cm$^{-1}$ (β-lactam); τ(CDCl$_3$) values include 4.06 (7H), 4.19 (—CH=CH—C≡C—), 4.91 (6H), 5.91 (—OCH$_3$), 8.02 (C≡C—CH$_3$).

(b) (6R,7R)-7-[(Z)-2-(methoxyimino)-2-(2-furyl)acetamido]-3-[(E)-pent-1-en-3-ynyl]ceph-3-em-4-carboxylic acid The title compound (318 mg) was prepared as a foam from the product of stage (a) (487 mg) according to the method of Example 18(b) and exhibited; $\nu_{max}$ (Nujol) 3260 (NH), 2204 (C≡C), 1778 cm$^{-1}$ (β-lactam); τ(DMSO-d6) values include 0.17 (NH), 2.89 (—CH=CH—C≡C), 3.89 (—CH=CH—C≡C), 4.14 (7H), 4.72 (6H), 6.03 (—OCH$_3$) 7.94 (—C≡C—CH$_3$).

EXAMPLE 20

(a) Diphenylmethyl(6R,7R)-7-[(Z)-2-(2-t-butoxycarbonylprop-2-oxyimino)-2-(2-tritylaminothiazol-4-yl)acetamido]-3-[(E)-pent-1-en-3-ynyl]ceph-3-em-4-carboxylate The title compound (959 mg) was prepared as a foam from (Z)-2-(2-t-butoxycarbonylprop-2-oxyimino)-2-(2-tritylaminothiazol-4-yl)acetic acid (1.143 ml) and the product of Preparation 7 (827 mg) according to the method of Example 16(a) and exhibited; $\nu_{max}$ (CHBr$_3$)

3400, 3260 (NH), 2220 (C≡C), 1790 cm$^{-1}$ (β-lactam); τ(CDCl$_3$) values include 1.93 (CONH), 4.03 (7H), 4.24 (—CH═CH—C≡C), 4.94 (6H), 8.03 (C≡C—CH$_3$) 8.47, 8.52 (C(CH$_3$)$_2$).

(b)

(6R,7R)-7-[(Z)-2-(2-carboxyprop-2-oxyimino)-2-(2-aminothiazol-4-yl)-acetamido]-3-[(E)-pent-1-en-3-ynyl]-ceph-3-em-4-carboxylic acid TFA (8 ml) was added to a stirred solution of the product of stage (a) (914 mg) in anisole (2 ml) at 5°. After 15 min at 5° and 30 min at 20° the reaction mixture was added dropwise to rapidly stirred water (200 ml). After 5 min the aqueous phase was washed with ether (4×100 ml), concentrated to 150 ml and freeze dried to give a pale yellow foam (20 mg). The ether extracts were evaporated and the residue treated with TFA (2 ml) as above to give a pale yellow foam (80 mg). The ether extracts were concentrated to 2 ml and added dropwise to rapidly stirred diisopropyl ether (150 ml). The resulting precipitate was collected by filtration, washed with ether (×5) and dried in vacuo to give an off white powder (90 mg). The above three fractions were identical by reverse phase t.l.c. (acetronitrile:water; 1:4) and were combined to give the title compound as a solid (196 mg); ν$_{max}$(Nujol) 3300 (NH), 1778 cm$^{-1}$ (β-lactam); τ(DMSO-d6) values include 0.56 (CONH), 2.94 (—CH═CH—C≡C), 3.93 (—CH═CH—C≡C—), 4.13 (7H), 4.75 (6H), 7.99 (C≡C—CH$_3$), 8.50 (—C(CH$_3$)$_2$).

EXAMPLE 21

(a)

Diphenylmethyl(2R,6R,7R)-7-(2-thienyl)acetamido-3-[(1-hydroxy)but-3-ynyl]ceph-2-em-4-carboxylate A solution of freshly prepared propargyl magnesium bromide (50 mmol) in THF (50 ml) was added dropwise over 30 min to a stirred solution of diphenylmethyl (2R,6R,7R)-3-formyl-7-(2-thienylacetamido)ceph-2-em-4-carboxylate (2.59 g) in THF (30 ml) at −70°, under nitrogen. After 1 h at −70° the reaction was quenched by the addition of saturated ammonium chloride solution (50 ml). On warming to 0° the reaction mixture was partitioned between ethyl acetate (150 ml) and 1M hydrochloric acid (150 ml). The layers were separated and the aqueous phase extracted with ethyl acetate (2×50 ml). The combined organic extracts were washed with water, sodium bicarbonate solution and brine (200 ml of each), and dried (sodium sulphate). The solvent was evaporated and the residue purified by chromatography (150 g silica gel). Elution with ethyl acetate:petroleum ether (1:1) afforded the title compound as a foam (1.25 g); τ(CDCl$_3$) values include 3.54 (NH), 4.44, 4.46 (7H, two diastereoisomers), 4.86, 4.88 (6H), 4.75, 4.91 (4H), 6.16 (—CH$_2$CO), 7.56 (—CH$_2$C≡C), 8.00 (C≡C—H).

(b)

Diphenylmethyl(2R,6R,7R)-7-(2-thienyl)acetamido-3-[(E and Z)-but-1-en-3-ynyl]ceph-2-em-4-carboxylate The product of Stage (a) was added to a stirred solution of methanesulphonic anhydride (40 mg, 0.52 mmol) in dichlormethane (2 ml) at 0°. After 1 min, triethylamine (0.15 ml, 1.05 mmol) was added. After 30 min at 0° the reaction mixture was diluted with ethyl acetate (50 ml), washed with 2M hydrochloric acid, water, sodium bicarbonate solution and brine (50 ml of each), and dried (sodium sulphate). The solvent was evaporated and the residue purified by chromatography (15 g silica gel). Elution with ethyl acetate:petroleum ether (1:2) afforded the title compound as a foam (85 mg); λ$_{max}$ (EtOH) 302.5 nm (ε21,400); τ(CDCl$_3$) values include 3.51 (—CH═CH—C≡C), 4.42 (—CH═CH—C≡C), 4.47 (7H), 4.78 (6H), 4.81 (4H), 6.18 (—CH$_2$—CO), 7.01 (C≡C—H).

The (E) and (Z) isomers of this compound could be separated using the usual techniques. The Δ2 isomers could then be converted into the corresponding Δ3 isomers and then be deprotected using conventional techniques to afford either (6R,7R)-7-(2-thienyl)acetamido-3-[(E)-but-1-en-3-ynyl]ceph-3-em-4-carboxylic acid or its corresponding (Z) isomer.

EXAMPLE 22

(a)

Diphenylmethyl(6R,7R)-7-[(Z)-2-(t-butoxycarbonylmethoxyimino)-2-(2-tritylaminothiazol-4-yl)acetamido]-3-[(E)-pent-1-en-3-ynyl]ceph-3-em-4-carboxylate To a stirred solution of dimethylformamide (2.5 ml) in dichloromethane (50 ml) cooled to −15° under nitrogen, was added a solution of oxalyl chloride (1.20 ml) in dichloromethane (15 ml) dropwise over 5 min, and the resultant suspension allowed to warm to −5° over 10 min. The mixture was re-cooled to −10° and (Z)-2-(2-t-butoxycarbonylmethoxyimino)-2-(2-tritylaminothiazol-4-yl)acetic acid (6.40 g) added as a slurry in dichloromethane (3 ml). The resultant solution was stirred at −5° for 30 min and re-cooled to −10°. To a stirred solution of diphenylmethyl (6R,7R)-7-amino-3-[(E)-pent-1-en-3-ynyl]ceph-3-em-4-carboxylate, hydrochloride (5.50 g) and N,N-dimethylaniline (6.0 ml) in dichloromethane (45 ml) cooled to −25°, under nitrogen was rapidly added the solution of activated side chain acid and the resultant solution allowed to warm to 0° over 30 min and then to 21° over 1 hour. The reaction mixture was partitioned between 2M aqueous hydrochloric acid (500 ml) and dichloromethane (900 ml). The organic phase was separated off, washed sequentially with 2M aqueous hydrochloric acid (500 ml), water (500 ml), saturated aqueous sodium bicarbonate (500 ml) and brine (500 ml), dried over magnesium sulphate and concentrated to give a foam (11.90 g), which was chromatographed on Merck Kieselgel 60 (70–230 mesh) (500 g) using an eluent mixture of dichloromethane:ethyl acetate (19:1). Appropriate fractions were combined, concentrated to 200 ml, washed sequentially with 2M aqueous hydrochloric acid (100 ml), water (100 ml) and brine (100 ml), dried over magnesium sulphate and concentrated in vacuo to give the title compound as a foam (9.05 g); [α]$_D^{21}$ −107° (c 0.94 in DMSO); ν$_{max}$ (ethanol) 324 nm (ε28 500); ν$_{max}$(CHBr$_3$) and τ(CDCl$_3$) values similar to Example 1(c).

(b)

(6R,7R)-7-[(Z)-2-(2-Aminothiazol-4-yl)-2-(carboxymethoxyimino)acetamido]-3-[(E)-pent-1-en-3-ynyl]ceph-3-em-4-carboxylic acid To a solution of the product of stage (a) (3.37 g) in anisole (6 ml) was added trifluoroacetic acid (25 ml) and the mixture stirred at 21° for 1 hour. Water (5 ml) was added and stirring at 21° continued for a further 45 min. The solution was added dropwise to rapidly stirred isopropyl ether (600 ml) and the resultant precipitate filtered off, washed with isopropyl ether (2×20 ml) and dried to give a powder (1.63 g). This was treated with saturated aqueous bicarbonate (50 ml) and water (100 ml). When effervescence ceased, the resultant suspension was warmed at <40° to give a solution which was chromatographed on Diaion HP-20 resin (100 g), eluting sequentially with water (500 ml), 2% (v/v) aqueous methanol (300 ml) and 5% (v/v) aqueous methanol (700 ml). Appropriate fractions were combined, concentrated to 500 ml and the solution acidified to pH 3.2 with 36% (w/w) aqueous hydrochloric acid. The resultant suspension was extracted with ethyl acetate:tetrahydrofuran (2:1) (300 ml) and the phases separated. The aqueous phase was saturated with sodium chloride and re-extracted with ethyl acetate:tetrahydrofuran (2:1) (2×300 ml). The combined organic extracts were washed with brine (200 ml) and the brine wash back-extracted with ethyl acetate:tetrahydrofuran (2:1) (2×150 ml). The combined organic extracts were dried over sodium sulphate and concentrated to a solid which was triturated with diethyl ether (40 ml), filtered off and dried to give the title compound as a powder (1.16 g); $[\alpha]_D^{21}$ −120° (c 0.51 in DMSO); $\lambda_{max}$ (ethanol) 232.5 nm ($\epsilon$18 700) and 315 nm ($\epsilon$31 100); $\nu_{max}$ (Nujol) 3700–2100 (NH$_2$, NH+OH), 2215 (—C≡C—), 1762 ($\beta$-lactam), 1730 (—CO$_2$H), 1675 cm$^{-1}$ (—CONH—); $\tau$(DMSO-d$_6$) 0.44 (—CONH—) 2.74 (NH$_2$), 2.88 (—CH=CH—C≡C—CH$_3$), 3.15 (thiazolyl), 3.91 (—CH=CH—C≡C—CH$_3$), 4.14 (7H), 4.75 (6H), 5.36 (—OCH$_2$CO$_2$—), 6.13, 6.38 (2—CH$_2$), 7.97 (—C≡C—CH$_3$); HPLC 93.2% pure.

EXAMPLE 23

(6R,7R)-7-[(Z)-2-(2-Aminothiazol-4-yl)-2-(carboxymethoxyimino)acetamido]-3-[(E)-pent-1-en-3-ynyl]ceph-3-em-4-carboxylic acid, sodium salt (6R,7R)-7-[(Z)-2-(2-Aminothiazol-4-yl)-2-(carboxymethoxyimino)acetamido]-3-[(E)-pent-1-en-3-ynyl]-ceph-3-em-4-carboxylic acid, trifluoroacetate salt (4.59 g) was treated with saturated aqueous sodium bicarbonate (50 ml) and water (50 ml). When effervescence ceased, the resultant precipitate was filtered off, washed sequentially with water (2 ml) and diethyl ether (3×5 ml) and dried to give the title compound as fine needles (0.22 g) m.p.>230°; $[\alpha]_D^{21}$ −75.1° (c 0.42 in H$_2$O); $\lambda_{max}$ (pH 6 buffer) 232.5 nm ($\epsilon$16 500), 312.5 nm ($\epsilon$30 200); $\nu_{max}$ (Nujol) 3700–2500 (NH$_2$, NH+OH), 2200 (—C≡C—), 1752 ($\beta$-lactam), 1688, 1535 (—CONH—), 1600 cm$^{-1}$ (—CO$_2$—); $\tau$(D$_2$O) 2.96 (thiazolyl), 3.07 (—CH=CH—C≡C—CH$_3$), 4.19 (7H), 4.20 (—CH=CH—C≡C—CH$_3$), 4.76 (6H), 5.44 (—OCH$_2$CO$_2$—), 6.32, 6.43 (2—CH$_2$), 8.05 (—C≡C—CH$_3$).

EXAMPLE 24

(a)
Diphenylmethyl(2'R,6R,7R)-7-(2'-t-Butoxycarbonylamino-2'-phenylacetamido)-3-[(E)-pent-1-en-3-ynyl]-ceph-3-em-4-carboxylate To a solution of the product of Preparation 8 (207 mg) in dichloromethane (8 ml) were added 2-t-butoxycarbonylamino-2-phenyl acetic acid (121 mg), 1-hydroxy benzotriazole hydrate (115 mg) and dicyclohexylcarbodiimide (155 mg). The mixture was stirred at 23° for 17 h. The precipitated solid was filtered off and washed with dichloromethane (2×5 ml) and the combined filtrate and washings were washed sequentially with water (10 ml), saturated aqueous sodium bicarbonate solution (2×10 ml) and water (2×10 ml), dried over magnesium sulphate and evaporated to dryness. The solid obtained was chromatographed on silica gel (25 g) eluting with a 15:1 mixture of dichloromethane and ethyl acetate. Appropriate fractions were combined and evaporated to give the title ester as a solid (195 mg), m.p. 178° to 180° $\lambda_{max}$ (EtOH) 326.5 nm ($\epsilon$26 880).

(b)
(2R',6R,7R)-7-(2'-Amino-2'-phenylacetamido)-3-[(E)-pent-1-en-3-ynyl]-ceph-3-em-4-carboxylic Acid, Trifluoroacetate Salt To a mixture of the product of stage (a) (167 mg) and anisole (0.3 ml) cooled in ice was added trifluoroacetic acid (2 ml). The solution was stirred in ice for 1 h and then it was added to stirred diisopropyl ether (70 ml). The precipitated solid (41 mg) was filtered off and dried. The filtrate was concentrated under vacuum and the residue was triturated with ether (50 ml). The resulting solid (52 mg) was filtered off. Both batches of product were combined, triturated with ether (5 ml), filtered off and dried to give the title compound (88 mg), $\lambda_{max}$ (EtOH) 332.5 nm ($\epsilon$21 580), $\nu_{max}$ (Nujol) 3700 to 2100 (NH, OH, NH$_3^+$), 2220 (C≡C), 1772 (azetidin-2-one C=O), 1700 (carboxylic acid C=O), 1675 (amide C=O), 1570 (carboxylate C=O) and 725 cm$^{-1}$ (phenyl), $\tau$(DMSO-d$_6$) 0.42 (NH), 2.3 to 2.8 (phenyl protons and NH$_3^+$), 2.94 (d, J 17 Hz, CH=CH—C≡C) 4.03 (d, J 17 Hz, CH=CH—C≡C), 4.21 (C$_7$—H), 4.89 (d, J 5 Hz, C$_6$H), 4.93 (PhCH), 6.25 and 6.51 (ABq, J 18 Hz, C$_2$—H$_2$) and 7.99 (CH$_3$).

The following examples illustrate pharmaceutical formulations according to the invention.

EXAMPLE A

Dry powder for Injection

Fill sterile (6R,7R)-7-[(Z)-2-(2-aminothiazol-4-yl)-2-(carboxymethoxyimino)acetamido]-3-[(E)-pent-1-en-3-ynyl]ceph-3-em-4-carboxylic acid, sodium salt aseptically into glass vials, such that each vial contains an amount equivalent to 1 g of the anhydrous cephalosporin acid. Purge the vial headspaces with sterile nitrogen; close the vials using rubber discs, or plugs, and metal overseals (applied by crimping). The product may be constituted by dissolving in water for injections or other suitable sterile vehicle shortly before administration.

EXAMPLE B

| Tablet for oral administration | mg/tablet |
|---|---|
| Cephalosporin | 250 |
| Sodium starch glycollate | 5 |
| Microcrystalline cellulose | 45 |
| Sodium lauryl sulphate | 3 |

Sieve (6R,7R)-7-[(Z)-2-(2-aminothiazol-4-yl)-2-(carboxymethoxyimino)acetamido]-3-[(E)-pent-1-en-3-ynyl]ceph-3-em-4-carboxylic acid and the microcrystalline cellulose through a 40 mesh screen. Sieve the sodium starch glycollate and sodium lauryl sulphate through a 60 mesh screen. Blend the powders together in a suitable blender until homogenous. Compress on appropriate punches on an automatic tablet machine. The tablets may be covered in a thin polymer coat applied by the usual film coating techniques. A pigment may be included in the film coat.

Other compounds of the invention may be formulated in a similar manner.

We claim:
1. A compound of formula (I):

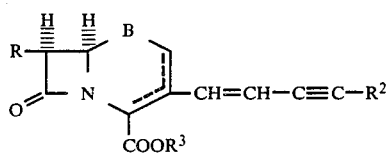

wherein

R represents NH$_2$— or an acylated amino group R$^1$NH—, wherein R$^1$ is an acyl group selected from the group consisting of:
(i) a group of formula R$^a$CH$_2$CO—, where R$^a$ is a 5- or 6-membered heterocyclic aryl group having one or more heteroatoms selected from S, N and O in the ring, said heterocyclic group being unsubstituted or substituted by one or more halogen atoms, or nitro, hydroxyl, amino, C$_{1-6}$alkyl, C$_{1-6}$alkoxy or C$_{2-6}$acyloxy groups;
(ii) a group of formula

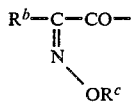

where R$^b$ is a phenyl group or a 5- or 6-membered heterocyclic aryl group having one or more heteroatoms selected from S, N and O in the ring, said phenyl or heterocyclic groups being unsubstituted or substituted by one or more halogen atoms, or nitro, hydroxyl, amino, C$_{1-6}$alkyl, C$_{1-6}$alkoxy or C$_{2-6}$acyloxy groups, and R$^c$ is a hydrogen atom, a C$_{1-4}$alkyl, C$_{2-4}$alkenyl, C$_{2-4}$alkynyl, C$_{3-6}$cycloalkyl, C$_{3-6}$cycloalkyl-C$_{1-4}$alkyl or C$_{2-6}$alkanoyl group, a phenyl or benzyl group, a 5- or 6-membered heterocyclic aryl group containing at least one heteroatom selected from S, N and O, or a corresponding aryl heterocyclicmethyl group, the group R$^c$ being unsubstituted or substituted by hydroxyl, C$_{1-6}$alkoxy, amino, methylamino, dimethyl-amino, nitro, carbamoyl, methyl- or dimethyl-carbamoyl, carboxyl, esterified carboxyl or cyano, or by halogen; and
(iii) a group of formula

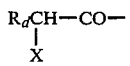

where R$^d$ is defined as for R$^a$ or is a phenyl, 4-hydroxy-phenyl, cyclohexa-1,4-dien-1-yl, naphthyl or benzothienyl group and X is an amino, hydroxyl, carboxyl or esterified carboxyl group;
R$^2$ represents a hydrogen or halogen atom or a C$_{1-4}$alkyl, phenyl, furyl, carboxyl or C$_{2-5}$alkoxycarbonyl group;
R$^3$ represents a hydrogen atom or a carboxyl blocking group;
B is >S or >S→O ($\alpha$- or $\beta$-) and the dotted line bridging the 2-, 3- and 4-positions indicates that the compound is a ceph-2-em or ceph-3-em compound, and salts, solvates and esters thereof.

2. A compond as claimed in claim 1 having the formula (Ib):

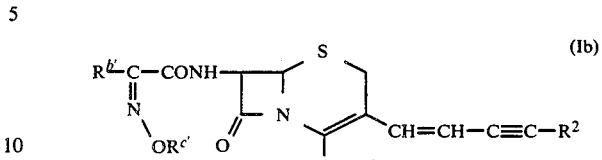

(wherein R$^{b'}$ represents a thiazolyl, thiadiazolyl, furyl, thienyl or pyrimidyl group optionally substituted by one or more substituents selected from amino or halo (chloro, bromo or iodo), R$^{c'}$ represents a hydrogen atom or a C$_{1-4}$alkyl, C$_{2-4}$alkenyl, C$_{2-4}$alkynyl, C$_{3-6}$cycloalkyl or C$_{3-6}$cycloalkyl-C$_{1-4}$alkyl group optionally substituted by carbamoyl, methyl-carbamoyl, dimethylcarbamoyl, carboxyl, C$_{2-5}$alkoxycarbonyl or halo and R$^2$ represents a hydrogen atom or a C$_{1-4}$alkyl, phenyl, carboxyl or C$_{2-5}$alkoxycarbonyl group), and non-toxic salts, solvates and non-toxic metabolically labile esters thereof.

3. A compound as claimed in claim 1 having the formula (Ic):

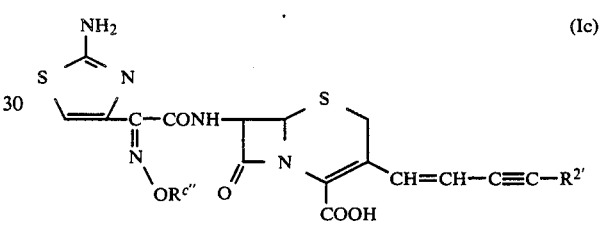

(wherein R$^{c''}$ represents a hydrogen atom or a methyl, ethyl, carboxy-methyl, 2-carboxyprop-2-yl, carbamoylmethyl or methoxycarbonylmethyl group and R$^{2'}$ represents a hydrogen atom or a C$_{1-4}$alkyl group) and non-toxic salts, solvates and non-toxic metabolically labile esters thereof.

4. A compound as claimed in claim 1, wherein the 3-substituent on the cephalosporin nucleus is in the trans configuration.

5. A compound as claimed in claim 1 selected from the group consisting of:
(6R,7R)-7-[(Z)-2-(2-aminothiazol-4-yl)-2-(carboxymethoxyimino)acetamido]-3-[(E)-hex-1-en-3-ynyl]ceph-3-em-4-carboxylic acid; and
(6R,7R)-7-[(Z)-2-(2-aminothiazol-4-yl)-2-(carboxymethoxyimino)acetamido]-3-[(E)-but-1-en-3-ynyl]ceph-3-em-4-carboxylic acid;

6. (6R,7R)-7-[(Z)-2-(2-aminothiazol-4-yl)-2-(carboxymethoxyimino)acetamido]-3-[(E)-pent-1-en-3-ynyl]-ceph-3-em-4-carboxylic acid, and non-toxic salts, solvates or non-toxic methabolically labile esters thereof.

7. Pharmaceutical compositions comprising, as active ingredients, at least one compound as claimed in claim 1 in association with one or more physiologically acceptable carriers and/or excipients.

8. A method of combating bacterial infections in human and animal subjects wherein an antibacterially effective amount of an antibiotic compound as claimed in claim 1 is administered prophylactically or therepeutically to the said subject.

* * * * *